United States Patent [19]

Mayeux et al.

[11] Patent Number: 5,922,556
[45] Date of Patent: Jul. 13, 1999

[54] PARKINSON'S DISEASE TESTS

[75] Inventors: Richard Mayeux; Joseph Graziano, both of Hastings-on-Hudson; Greg Freyer, Ardsley, all of N.Y.

[73] Assignee: The Trustees of Columbia University in the City of New York, New York, N.Y.

[21] Appl. No.: 08/887,798

[22] Filed: Jul. 3, 1997

[51] Int. Cl.⁶ .............................. C12Q 1/34; C12Q 1/00; G01N 33/48

[52] U.S. Cl. ............................ 435/18; 435/71; 435/4; 436/63

[58] Field of Search ................................ 435/18, 7.1, 4, 435/71; 436/63

[56] References Cited

PUBLICATIONS

Ames (1983) Dietary carcinogens and anticarcinogens: oxygen radicals and degenerative diseases, Science 221, 1256–1264 (Exhibit 2).
Beinert and Kennedy (1993) Aconitase, a two–faced protein: enzyme and regulatory factor, FASEB J 7, 1442–1449 (Exhibit 3).
Connor (1993) Cellular and regional maintenance of iron homeostasis in the brain: normal and diseased states, In: Riederer and Youdim, Eds. Iron In Central Nervous System Disorders, New York, Springer–Verlag Wien, pp. 1–18 (Exhibit 4).
Coyle and Puttfarcken (1993) Oxidative stress, glutamate, and neurode–generative disorders, Science 262, 689–695 (Exhibit 5).
Fahn and Cohen (1992) The oxidant stress hypothesis in Parkinson's disease: evidence supporting it, Ann Neurol 32, 804–812 (Exhibit 6).
Gray et al (1996) Translational regulation of mammalian and Drosophila citric acid cycle enzymes via iron–responsive elements, Proc Natl Acad Sci USA 93, 4925–4930 (Exhibit 7).
Hoehn and Yahr (1967) Parkinson's onset, progression and mortality, Neurology 17, 427–442 (Exhibit 8).
Hughes et al (1992) What features improve the accuracy of clinical diagnosis in Parkinson's disease: a clinicopathologic study, Neurology 42, 1142–1146 (Exhibit 9).
Hughes et al (1992) Accuracy of clinical diagnosis of idiopathic Parkinson's disease: a clinico–pathological study of 100 cases, J Neurol Neurosurg Psychiatry 55, 181–184 (Exhibit 10).
Jafrey et al (1994) The iron–responsive element binding protein: a target for synaptic actions of nitric oxide, Proc Natl Acad Sci USA 91, 12994–12998 (Exhibit 11).
Janetzky et al (1994) Unaltered aconitase activity, but decreased complex I activity in substantia nigra pars compacta of patients with Parkinson's disease, Neurosci Lett 169, 126–128 (Exhibit 12).
Javitch et al (1985) Parkinsonism–inducing neurotoxin MPTP: uptake of the metabolite MPP+ by dopamine neurons explains selective toxicity, Proc Natl Acad Sci USA 82, 2173–2177 (Exhibit 13).

(List continued on next page.)

*Primary Examiner*—Louise N. Leary
*Attorney, Agent, or Firm*—John P. White; Cooper & Dunham LLP

[57] ABSTRACT

This invention provides methods of determining the susceptibility to Parkinson's disease of a subject and of diagnosing Parkinson's disease in a subject which comprises detecting in a sample from the subject the presence of a composition of matter, which composition comprises a band having an apparent molecular weight of about 83 kilodaltons as determined by denaturing polyacrylamide gel electrophoresis, is capable of being specifically detected by an antibody directed to mitochondrial aconitase hydroxylase, and has greater electrophoretic mobility than the corresponding unaltered composition as determined by non-denaturing polyacrylamide gel electrophoresis.

6 Claims, 13 Drawing Sheets

OTHER PUBLICATIONS

Klausner and Rouault (1993) A double life: cytosolic aconitase as a regulatory RNA binding protein, Mol Cell Biol 4, 1–5 (Exhibit 15).

Klausner er al (1993) Regulating the fate of mRNA: the control of cellular iron metabolism, Cell 72, 19–28 (Exhibit 16).

Logroscino et al (1996) Dietary lipids and antioxidants in Parkinson's disease: a population–based, case–control study, Ann Neurol 39, 89–94 (Exhibit 17).

Luft (1994) The development of mitochondrial medicine, Proc Natl Acad Sci USA 91, 8731–8738 (Exhibit 18).

Mann et al (1994) Complex I, iron, and ferritin in Parkinson's disease substantia nigra, Ann Neurol 36, 876–881 (Exhibit 19).

Mayeux et al (1995) The frequency of idiopathic Parkinson's disease among middle–aged and elderly black, hispanic and white men and women in northern Manhattan 1988 to 1993, Am J Epidemiol 142, 820–827 (Exhibit 20).

Marder et al (1996) Risk of Parkinson's disease among first–degree relatives: a community–based study, Neurology 47, 155–160 (Exhibit 21).

Payami et al (1994) Increased risk of Parkinson's disease in parents and siblings of patients, Ann Neurol 36, 659–661 (Exhibit 22).

Polymeropoulos et al (1996) Mapping of a gene for Parkinson's disease to chromosome 4q21–q23, Science 274, 1197–1199 (Exhibit 23).

Polymeropoulos et al (Jun. 27, 1997) Mutation in the alpa synuclein gene identified in families with Parkinson's disease, Science 276, 2045–2047 (Exhibit 24).

Slaughter et al (1975) Aconitase polymorphism in man, Ann Hum Genet 39, 193,–202 (Exhibit 25).

Stern (1978) The clinical characteristics of Parkinson's disease and parkinsonian syndromes: diagnosis and assessment, In: Stern and Hurtig, Eds., The Comprehensive Management of Parkinson's Disease, New York, PMA Publishing Corp., pp. 34–39 (Exhibit 26).

Swerdlow et al (1996) Origin and functional consequences of the Complex I defect in Parkinson's disease, Ann Neurol 40, 663–671 (Exhibit 27).

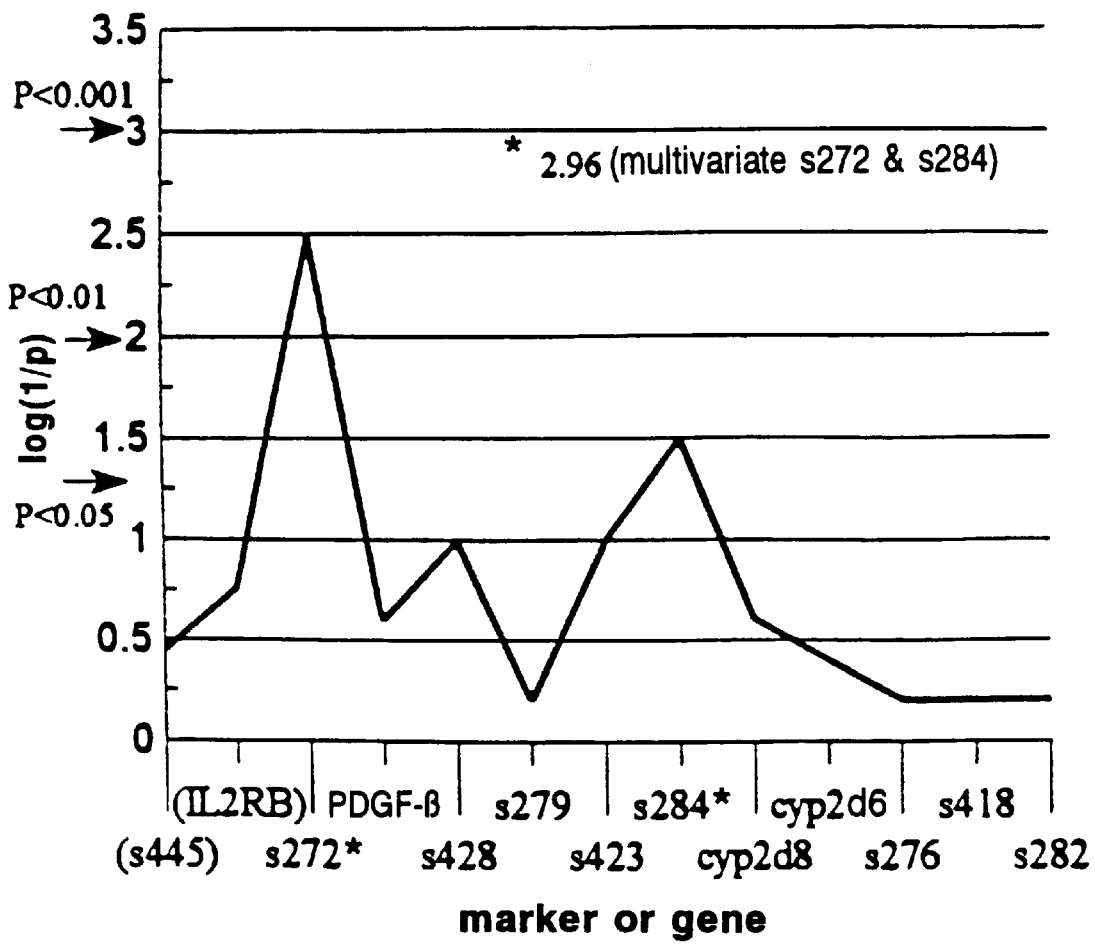

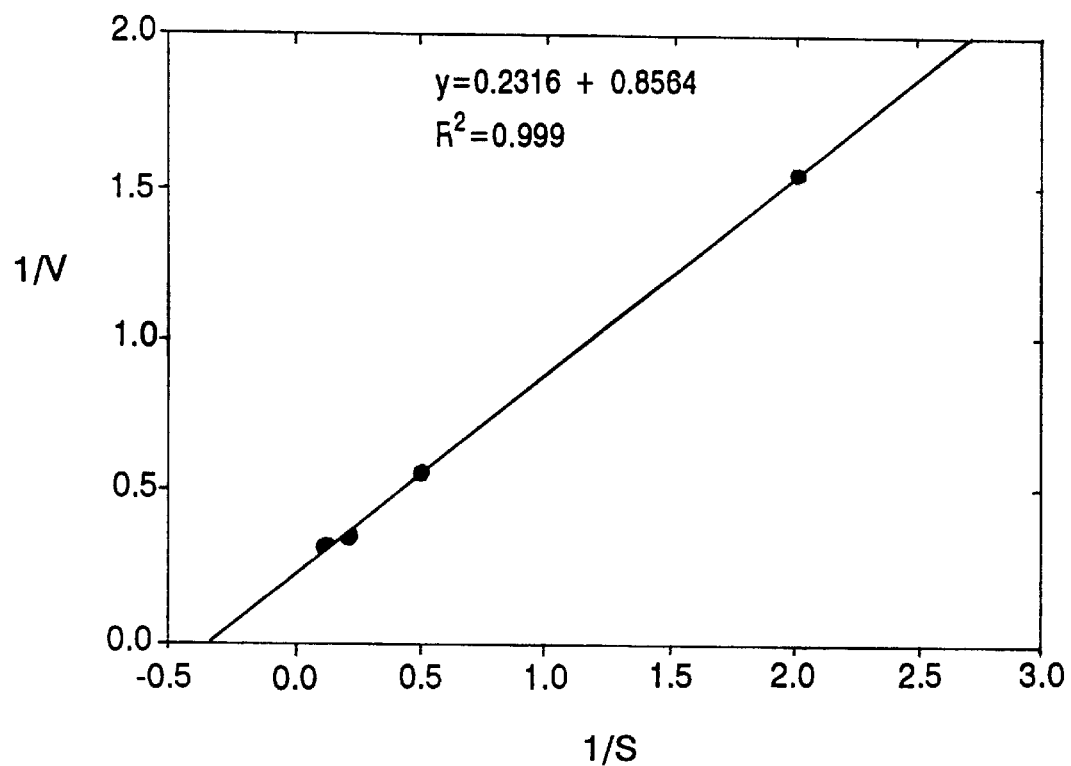

FIG. 8A

```
                  10                              30                              50
                                                                      M   A   P   Y   S   L   L
ACGGCAGCAAGGACAGCATCACATCTTTGTCAGTGCACAAAATGGCGCCCTACAGCCTAC
                                        /EXON 1

70                              90                              110
    V   T   R   L   Q   K   A   L   G   V   R   Q   Y   H   V   A   S   V   L   C
TGGTGACTCGGCTGCAGAAAGCTCTGGGTGTGCGGCAGTACCATGTGGCCTCAGTCCTGT
                                        /EXON 2

130                             150                             170
    Q   R   A   K   V   A   M   S   H   F   E   P   N   E   Y   I   H   Y   D   L
GCCAACGGGCCAAGGTGGCGATGAGCCATTTTGAGCCCAACGAGTACATCCATTATGACC 190                             210                             230
    L   E   K   N   I   N   I   V   R   K   R   L   N   R   P   L   T   L   S   E
TGCTAGAGAAGAACATTAACATTGTTCGCAAACGACTGAACCGGCCGCTGACACTCTCGG
                                        /EXON 3

250                             270                             290
    K   I   V   Y   G   H   L   D   D   P   A   S   Q   E   I   E   R   G   K   S
AGAAGATTGTGTATGGACACCTGGATGACCCCGCCAGCCAGGAAATTGAGCGAGGCAAGT 310                             330                             350
    Y   L   R   L   R   P   D   R   V   A   M   Q   D   A   T   A   Q   M   A   M
CGTACCTGCGGCTGCGGCCGGACCGTGTGGCCATGCAGGATGCGACGGCCCAGATGGCCA 370                             390                             410
    L   Q   F   I   S   S   G   L   S   K   V   A   V   P   S   T   I   H   C   D
TGCTCCAGTTCATCAGCAGCGGGCTGTCCAAGGTGGCTGTGCCATCCACCATCCACTGTG 430                             450                             470
    H   L   I   E   A   Q   V   G   G   E   K   D   L   R   R   A   K   D   I   N
ACCATCTGATTGAAGCCCAGGTTGGGGGCGAGAAAGACCTGCGCCGGGCCAAGGACATCA
                                                                        /EXON 4

490                             510                             530
    Q   E   V   Y   N   F   L   A   T   A   G   A   K   Y   G   V   G   F   W   K
ACCAGGAAGTTTATAATTTCCTGGCAACTGCAGGTGCCAAATATGGCGTGGGCTTCTGGA 550                             570                             590
    P   G   S   G   I   I   H   Q   I   I   L   E   N   Y   A   Y   P   G   V   L
AGCCTGGATCTGGAATCATTCACCAGATTATTCTGGAAAACTATGCGTACCCTGGTGTTC
                                        /EXON 5
```

FIG. 8B

```
          610                 630                 650
     L  I  G  T  D  S  H  T  P  N  G  G  G  L  G  G  I  C  I  G
     TTCTGATTGGCACTGACTCCCACACCCCCAATGGTGGCGGCCTTGGGGGCATCTGCATTG 670                 690                 710
     V  G  G  A  D  A  V  D  V  M  A  G  I  P  W  E  L  K  C  P
     GAGTTGGGGGTGCCGATGCTGTGGATGTCATGGCTGGGATCCCCTGGGAGCTGAAGTGCC 730                 750                 770
     K  V  I  G  V  K  L  T  G  S  L  S  G  W  S  S  P  K  D  V
     CCAAGGTGATTGGCGTGAAGCTGACGGGCTCCCTCTCCGGTTGGTCCTCACCCAAAGATG
        /EXON 6

790                 810                 830
     I  L  K  V  A  G  I  L  T  V  K  G  G  T  G  A  I  V  E  Y
     TGATCCTGAAGGTGGCAGGCATCCTCACGGTGAAAGGTGGCACAGGTGCAATCGTGGAAT 850                 870                 890
     H  G  P  G  V  D  S  I  S  C  T  G  M  A  T  I  C  N  M  G
     ACCACGGGCCTGGTGTAGACTCCATCTCCTGCACTGGCATGGCGACAATCTGCAACATGG
                                           /EXON 7

910                 930                 950
     A  E  I  G  A  T  T  S  V  F  P  Y  N  H  R  M  K  K  Y  L
     GTGCAGAAATTGGGGCCACCACTTCCGTGTTCCCTTACAACCACAGGATGAAGAAGTACC 970                 990                1010
     S  K  T  G  R  E  D  I  A  N  L  A  D  E  F  K  D  H  L  V
     TGAGCAAGACCGGCCGGGAAGACATTGCCAATCTAGCTGATGAATTCAAGGATCACTTGG
            /EXON 8

1030                1050                1070
     P  D  P  G  C  H  Y  D  Q  L  I  E  I  N  L  S  E  L  K  P
     TGCCTGACCCTGGCTGCCATTATGACCAACTAATTGAAATTAACCTCAGTGAGCTGAAGC
                                                       /EXON 9

1090                1110                1130
     H  I  N  G  P  F  T  P  D  L  A  H  P  V  A  E  V  G  K  V
     CACACATCAATGGGCCCTTCACCCCTGACCTGGCTCACCCTGTGGCAGAAGTGGGCAAGG 1150                1170                1190
     A  E  K  E  G  W  P  L  D  I  R  V  G  L  I  G  S  C  T  N
     TGGCAGAGAAGGAAGGATGGCCTCTGGACATCCGAGTGGGTCTAATTGGTAGCTGCACCA
                                                       /EXON 10

1210                1230                1250
     S  S  Y  E  D  M  G  R  S  A  A  V  A  K  Q  A  L  A  H  G
     ATTCAAGCTATGAAGATATGGGGCGCTCAGCAGCTGTGGCCAAGCAGGCACTGGCCCATG
```

FIG. 8C

```
          1270                1290                1310
      F  K  C  K  S  Q  F  T  I  T  P  G  S  E  Q  I  R  A  T  I
    GCTTCAAGTGCAAGTCCCAGTTCACCATCACTCCAGGTTCCGAGCAGATCCGCGCCACCA 1330                1350                1370
      E  R  D  G  Y  A  Q  I  L  R  D  L  G  G  I  V  L  A  N  A
    TTGAGCGGGACGGCTATGCACAGATCTTGAGGGATCTGGGTGGCATTGTCCTGGCCAATG
                        /EXON 11

1390                1410                1430
      C  G  P  C  I  G  Q  W  D  R  K  D  I  K  K  G  E  K  N  T
    CTTGTGGCCCCTGCATTGGCCAGTGGGACAGGAAGGACATCAAGAAGGGGGAGAAGAACA
                                /EXON 12

1450                1470                1490
      I  V  T  S  Y  N  R  N  F  T  G  R  N  D  A  N  P  E  T  H
    CAATCGTCACCTCCTACAACAGGAACTTCACGGGCCGCAACGACGCAAACCCCGAGACCC 1510                1530                1550
      A  F  V  T  S  P  E  I  V  T  A  L  A  I  A  G  T  L  K  F
    ATGCCTTTGTCACGTCCCCAGAGATTGTCACAGCCCTGGCCATTGCGGGAACCCTCAAGT
                          /EXON 13

1570                1590                1610
      N  P  E  T  D  Y  L  T  G  T  D  G  K  K  F  R  L  E  A  P
    TCAACCCAGAGACCGACTACCTGACGGGCACGGATGGCAAGAAGTTCAGGCTGGAGGCTC 1630                1650                1670
      D  A  D  E  L  P  K  G  E  F  D  P  G  Q  D  T  Y  Q  H  P
    CGGATGCAGATGAGCTTCCCAAAGGGGAGTTTGACCCAGGGCAGGACACCTACCAGCACC
                                    /EXON 14

1690                1710                1730
      P  K  D  S  S  G  Q  H  V  D  V  S  P  T  S  Q  R  L  Q  L
    CACCCAAGGACAGCAGCGGGCAGCATGTGGACGTGAGCCCCACCAGCCAGCGCCTGCAGC 1750                1770                1790
      L  E  P  F  D  K  W  D  G  K  D  L  E  D  L  Q  I  L  I  K
    TCCTGGAGCCTTTTGACAAGTGGGATGGCAAGGACCTGGAGGACCTGCAGATCCTCATCA 1810                1830                1850
      V  K  G  K  C  T  T  D  H  I  S  A  A  G  P  W  L  K  F  R
    AGGTCAAAGGGAAGTGTACCACTGACCACATCTCAGCTGCTGGCCCCTGGCTCAAGTTCC
    /EXON 15

1870                1890                1910
      G  H  L  D  N  I  S  N  N  L  L  I  G  A  I  N  I  E  N  G
    GTGGGCACTTGGATAACATCTCCAACAACCTGCTCATTGGTGCCATCAACATTGAAAACG
```

FIG. 8D

```
           1930                1950                1970
      K  A  N  S  V  R  N  A  V  T  Q  E  F  G  P  V  P  D  T  A
     GCAAGGCCAACTCCGTGCGCAATGCCGTCACTCAGGAGTTTGGCCCCGTCCCTGACACTG 1990                2010                2030
      R  Y  Y  K  K  H  G  I  R  W  V  V  I  G  D  E  N  Y  G  E
     CCCGCTACTACAAGAAACATGGCATCAGGTGGGTGGTGATCGGAGACGAGAACTACGGCG
              /EXON 16

2050                2070                2090
      G  S  S  R  E  H  A  A  L  E  P  R  H  L  G  G  R  A  I  I
     AGGGCTCGAGCCGGGAGCATGCAGCTCTGGAGCCTCGCCACCTTGGGGGCCGGGCCATCA 2110                2130                2150
      T  K  S  F  A  R  I  H  E  T  N  L  K  K  Q  G  L  L  P  L
     TCACCAAGAGCTTTGCCAGGATCCACGAGACCAACCTGAAGAAACAGGGCCTGCTGCCTC
                              /EXON 17

2170                2190                2210
      T  F  A  D  P  A  D  Y  N  K  I  H  P  V  D  K  L  T  I  Q
     TGACCTTCGCTGACCCGGCTGACTACAACAAGATTCACCCTGTGGACAAGCTGACCATTC 2230                2250                2270
      G  L  K  D  F  T  P  G  K  P  L  K  C  I  I  K  H  P  N  G
     AGGGCCTGAAGGACTTCACCCCTGGCAAGCCCCTGAAGTGCATCATCAAGCACCCCAACG
                              /EXON 18

2290                2310                2330
      T  Q  E  T  I  L  L  N  H  T  F  N  E  T  Q  I  E  W  F  R
     GGACCCAGGAGACCATCCTCCTGAACCACACCTTCAACGAGACGCAGATTGAGTGGTTCC 2350                2370                2390
      A  G  S  A  L  N  R  M  K  E  L  Q  Q  *
     GCGCTGGCAGTGCCCTCAACAGAATGAAGGAACTGCAACAGTGAGGGCAGTGCCTCCCCG 2410                2430                2450
     CCCCCCCCCGCTGGCGTCAAGTTCAGCTCCACGTGTGCCATCAGTGGATCCGATCCGTCC 2470                2490                2510
     AGCCATGGCTTCCTATTCCAAGATGGTGTGACCAGACATGCTTCCTGCTCCCCGCTTAGC 2530                2550                2570
     CCACGGAGTGACTGTGGTTGTGGTGGGGGGGTTCTTAAAATAACTTTTTAGCCCCCGTCT
```

FIG. 9

| exon name | exon num | 5' primer name | 5' primer sequence | 3' primer name | 3' primer sequence |
|---|---|---|---|---|---|
| B | 1 | ACEXBFC | CTATTTCTGCAAGTGTCTTTGGGC | ACEXBRC | CCGGGACAGGTACACGAGAAGTTGCA |
| C | 2 | ACOBEGFA | GCTGTGTTCCTTGTGGCTGCTTGTC | ACEXCR | TGCCACTATCACCAAGCATCCTTCAC |
| D | 3 | ACEXDFC | AGGTGAGGAGGTGGTGCAGTGAACAG | ACEXDRA | TGAGCCCTCTGCCCAGTCTTGCCCAC |
| E | 4 | ACEXEFB | GGTGGGGAGGCTTGGTGAGGGTCAC | ACEXERB | AGAGCATAAGAGCTGATGGATATGTC |
| H | 5 | ACEXHFB | ATTTTTGGTATTCTCGGCTGAGGGC | ACEXHRA | GCTTATTGGTCTCTACCTCCCTCCCA |
| 17 | 6 | ACEX17F | ATCCTGACTTCGTGGCTGGCACAGC | ACEX17R | AAGGCCACTTCACCGCTTCTACTCCC |
| 112 | 7 | ACEX112F | TGTGAAGATGCAGGTGGCCGCGTAGC | ACEX112R | CTTTCTCAGAGCCTCGGACGCCTGTC |
| 206 | 8 | ACEX206FA | TTCACGTGCTCATCCCCGTCCTTGTT | ACEX206R | TGAACTGCTGACCTCAACTGACCCAC |
| 286 | 9 | ACEX286F | AAGAGGCTGTCCCCGCTTCCAAGTT | ACEX286R | GTAGGCATAGGTGATTGTCTACAGCC |
| 386 | 10 | ACEX386F | TGCTCACTGTCTCCTCCTGACCCTTA | ACEX386R | ACTCAGCATGGGGTGGGGAGATGGG |
| 449 | 11 | ACEX449F | CCACCACATCACCCCTTCCCATCAGA | ACEX449R | ACTTCTGGGGCTCTGTACCCTGTG |
| 619 | 12 | ACEX619F | GGAACCCAGCTTATCTGTCCTCGGGA | ACEX619R | GCTGGGAAGGCCTGTAGCTCCTGGCT |
| 733 | 13 | ACEX733FB | CTAGGCTTTTGGTGAGAAGGAAGCAGCTCTGT | ACEX733R | GCCACACAGCAAACCAGCAAGCAG |
| 855 | 14 | ACEX855FB | TGCTAGTGAGAAGGAAGCAGCTCTGT | ACEX855RB | CTCCAGTTCATGGCCCTTCCCGATG |
| 1058 | 15 | ACEX1058FA | CCATGCCCTGACCTCTGTCTCTCTA | ACEX1058RA | TCGCCTCCTTCCAGTTTCCACTCCC |
| 1204 | 16 | ACEX1204F | TAGGGCCAGACAGGTGAGGACGGTGC | ACEX1204RB | AACTCAGCCACGGGCAGGGAGAGTG |
| 1391 | 17 | ACEX1391F | CCTAGTGAAAGGGAGCAGACAGGGC | ACEX1391RA | CTTTGCTTTCTCTGTGGGCCACCTG |
| Z | 18 | ACEXZFA | GTCCCCAGCAGTGCCCCTGTCTCCCTG | ACO8R2510 | ACAGTCACTCCGTGGGCTAAGCGGGGG | oligonucleotide primers used to amplify ACO2 gene exons.

FIG. 10

| EXON NUMBER | CURRENT EXON NAME | splice 5' to exon | exon length, bp | splice 3' to exon | intron length, bp (approx) |
|---|---|---|---|---|---|
| 1 | B | none? | 56 | CTGCAG/gtgagcgagc | ? |
| 2 | C | cttcttgcag/AAGCTT | 137 | CAAACG/gtaaggctgc | ? |
| 3 | D | ctccccacag/ACTGAA | 259 | CCAAAG/gtgagcagaa | 3695 |
| 4 | E | gtctcaatag/GACATC | 93 | CACCAG/gtaaagctgg | 2760 |
| 5 | H | tatttttcag/ATTATT | 159 | CCCAAG/gtgagggtgg | 230 |
| 6 | 17 | tcctgtccag/GTGATT | 151 | GCACTG/gtgaggaagg | 1560 |
| 7 | 112 | tgctccacag/GCATGG | 105 | GGGAAG/gtgagctggc | 810 |
| 8 | 206 | ttgatttcag/ACATTG | 92 | AGTGAG/gtgaggagac | 1580 |
| 9 | 286 | gtttcttcag/CTGAAG | 106 | GAGTGG/gtgagcacct | 2300 |
| 10 | 386 | aatgcaccag/GTCTAA | 158 | GGCTAT/gtgagtgccc | 220 |
| 11 | 449 | tccctggcag/GCACAG | 74 | GGACAG/gtaagagcat | 530 |
| 12 | 619 | gacctggcag/GAAGGA | 112 | CCAGAG/gtgagactgc | 865 |
| 13 | 733 | tccatttcag/ATTGTC | 123 | AAAGGG/gtgagcgcc | 230 |
| 14 | 855 | ggtgctgcag/GAGTTT | 156 | ATCAAG/gtaagcagca | 960 |
| 15 | 1058 | ccaccccaag/GTCAAA | 192 | TACAAG/gtgggtcaga | 700 |
| 16 | 1204 | tgcctgacag/AAACAT | 133 | TCCACG/gtgagctgga | 520 |
| 17 | 1391 | ctgctttcag/AGACCA | 122 | GGCAAG/gttaggcgcc | 390 |
| 18 | Z | ctccttgaag/CCCCTG | 134 to stop | NONE | none |

ACO2 gene exon and intron data.

PARKINSON'S DISEASE TESTS

The invention disclosed herein was made with Government support under Grant Nos. NS32527, RR00645, AG07232, and ES06831 from the National Institutes of Health, U.S. Department of Health and Human Services. Accordingly, the U.S. Government has certain rights to this invention.

Throughout this application, various publications are referenced by arabic numbers in parentheses. Full citations for these publications may be found listed at the end of the specification immediately preceding the claims. The disclosures of these publications in their entireties are hereby incorporated by reference in order to more fully describe the state of the art as known to those skilled therein as of the date of the invention described and claimed herein.

BACKGROUND OF THE INVENTION

Investigation of the genetics and epidemiology of idiopathic Parkinson's disease (IPD) have not identified an etiology. Risk of IPD is consistently higher among first-degree relatives of affected cases than among controls (1), but only a small number of families with multiple affected members have been reported suggesting an autosomal-dominant pattern with reduced penetrance (2). The concordance rate for IPD is higher for monozygotic than for dizygotic twin pairs in which one twin had onset before age 60 but not for pairs with a later age at onset (3). A cytochrome P450 gene, CYP2D6, was implicated as a candidate gene for IPD by some (5), but not all investigators (6), because the frequency of certain mutant alleles differed in IPD and controls (7,8). While each of these observations is compatible with a genetic etiology for IPD, the genetic contributions appear to be complex. The observations that occupational manganese exposure causes a form of parkinsonism (9,10) and that N-methyl-4-phenyl-1,2,3,6-tetrahydropyridine (MPTP) induces a form of parkinsonism in drug users (11) provide support for an environmental cause of IPD. Prevalence of IPD appears to be increased among individuals exposed to pesticides and related chemicals, especially MPTP-like compounds (12,13). IPD is also more prevalent among individuals raised in rural environments (14) or exposed to well water (15). Cigarette smoking (16) and the use of anti-oxidant vitamin supplements (17) remain unconfirmed "protective" factors. Thus, environmental factors related to IPD remain to be fully elucidated.

IPD as a disorder of iron metabolism. Of the total iron in an adult, 25% is a "reserve" stored in the cytoplasm as ferritin. The remaining iron is transported into mitochondria for synthesis of mitochondrial electron transport proteins or heme for production of cytochromes, hemoglobin or myoglobin (18). In IPD, iron accumulates in the substantia nigra (19–21) and receptors for the iron-transport protein lactoferrin are increased (22), while ferritin concentrations are reduced (23–25). This imbalance of "free" iron is believed to accelerate free radical formation and lipid peroxidation. It was recently found that lower concentrations of serum total iron binding capacity (TIBC), transferrin, iron and ferritin are detected in patients with IPD compared to controls. A paradoxical relationship between these parameters indicates a subtle, yet systemic, perturbation of iron metabolism. Low ferritin and serum iron suggested low iron stores, while the reduction in TIBC and transferrin, implied increased iron deposition.

These incongruous observations, at first, implied that the iron-regulatory proteins (IRP) which regulate the synthesis of iron-related proteins at the translation level (27) do not function normally in IPD, leading to increased iron entry into neurons, lower levels of iron in the extracellular compartment and a redistribution of free iron to the nigral intracellular compartment.

However, while attempting to identify the mechanism of this alteration in iron homeostasis, we discovered, by non-denaturing polyacrylamide gel electrophoresis of IPD and control sera, a shifted band which may comprise a variant of a nuclear-encoded mitochondrial gene, mitochondrial aconitase hydroxylase (ACO2). ACO2 is an iron-sulfur enzyme of the citric acid cycle responsible for the interconversion of citrate and isocitrate (FIG. 1). Because ACO2 is known to have relatively rare isoforms (28), we now infer that this protein, whose shift we have confirmed by Western blot using antibody, to bovine ACO2, may impart susceptibility to IPD via either mutation in the gene itself, mRNA splice variation, post-translational modification or non-covalent modification (e.g. a conformational change). Whatever it's molecular nature, the shifted band appears in 28/30 (93%) of IPD patients and in none of the controls. We have also recently discovered that the major isoform of human ACO2 in brain differs from that in placenta, suggesting brain-specific isoforms. Surprisingly, the genetic locus for ACO2 is on chromosome 22q13 near the CYP2D6 region (29). In parallel work, we excluded CYP2D6 as a candidate gene for IPD, but we did find evidence for an allelic association between IPD and dinucleotide repeat markers in the region near CYP2D6. That region includes the ACO2 gene. We now plan to sequence ACO2 in patients and controls to identify a potential mutation in IPD. We also recognize that a variant of ACO2 may be the result of a post-translational modification and not the result of a mutation or splice variant, or could be a consequence of an alteration induced by nitric oxide damage (31). As will be clear in our methods, we will not rely on any singular method of investigation to outline the putative role of ACO2 in the pathogenesis of IPD.

IPD as a disorder of mitochondria. Activity in complex I of the respiratory chain is reduced in the substantia nigra of patients with IPD (32, 33), particularly for subunits encoded in the mitochondrial genome (34, 35). MPTP inhibits the NADH-coenzyme Q reductase (complex I) activity in mitochondria (36–38). Swerdlow et al (39) have demonstrated that mitochondria from patients with IPD transfected into a cell line devoid of mitochondria gradually lose complex I activity. Mitochondrial DNA (mtDNA) is compact and encodes 13 enzymes of the respiratory chain complex (40). Mitochondria consume $O_2$ and in the process generate free radicals which react with membrane lipids, nucleic acids and proteins. The cause of neuronal death in IPD is unknown, but it has been proposed that oxidative damage to mtDNA may play a role (41). However, mtDNA mutations accumulate with age (42) and the consequent deficit in ATP production in certain critical neuronal populations could also indirectly contribute to the pathogenesis of IPD. Mitochondrial energy deficits have been postulated to contribute to neuronal injury via excitotoxic mechanisms that include oxygen free radical formation (43), glutamate (44) and nitric oxide toxicity (45). Even under normal circumstances, iron accumulates in the substantia nigra as a cofactor required for dopamine synthesis. However, excess iron accumulates in IPD (46); this likely shifts iron into mitochondria, leading to oxidation of mitochondrial nucleic acids.

Evidence that IPD is associated with higher energy expenditure is supported by recent findings (47) and has been confirmed by others (48). IPD patients consume 25% more calories than controls, suggesting a systemic alteration in energy metabolism. Yet during the course of the illness IPD patients typically lose weight while becoming less physically active. It is possible that the dietary alterations could have a role in the pathogenesis of IPD by contributing to lipid peroxidation (49, 50). Alternatively, changes in diet may actually be a response to the higher metabolic rate induced by disease.

If ACO2 plays a central role in the pathogenesis of IPD, as we believe, how can we explain its influence on both energy and iron metabolism in IPD? Cytosolic aconitase (ACO1) controls iron homeostasis by modulation of the translation of an array of iron proteins including transferrin, transferrin receptor, ferritin, d-ALA-synthetase and even ACO2, all of which are encoded in the nuclear genome (27, 51, 52). Synthesis of these proteins is controlled by cytoplasmic iron status. The mRNAs of each of these proteins contain a non-translated loop of nucleotides referred to as an iron-binding element or iron-response element (IRE). The consensus stem of the IRE contains 21 nucleotides, only one of which is highly conserved. The apex of the loop contains six nucleotides; the first five are highly conserved (CAGUG) and the sixth is usually a pyrimidine (53, 54). Translation of ferritin, transferrin receptor and ACO2 mRNA is largely controlled by an iron-binding cytosolic protein (known as IRE-BP, IRP1 or ACO1) which binds to the IRE within these mRNAs when cytoplasmic iron is insufficient. Amino acid sequencing of IRP1 (ACO1) revealed 57% homology with ACO2 (55). Both ACO1 and ACO2 contain a 4Fe-4S cubane cluster which serves as the enzymatic binding site for citrate (FIG. 2, Part A). When iron is insufficient, ACO1 assumes a 3Fe-4S configuration, loses its enzymatic activity and is transformed into an mRNA-binding-protein which then attaches to the mRNA IRE (FIG. 2, Part B). For example, binding of ACO1 to the transferrin receptor mRNA IRE increases the synthesis of the transferrin receptor protein; binding to the mRNA IRE of ferritin stops its synthesis. Thus, ACO1 is able to respond to iron deficiency and regulate iron homeostasis. We postulate that ACO2 plays a similar role by regulating the synthesis of proteins encoded by the mitochondrial genome. While the gene for ACO2 itself is in the nuclear genome, many proteins involved in mitochondrial energy metabolism, e.g. those of complex I, reside in the mitochondrial genome. We have already searched the mitochondrial genome for evidence of an IRE comparable to those of ferritin and transferrin receptor, as described above, but none exists. We propose that the mRNAs of proteins encoded in the mitochondrial genome may have a different IRE structure for specifically binding ACO2. In this manner, ACO2 may regulate the synthesis of proteins of complex I and may, in turn, regulate mitochondrial iron uptake from the cytoplasm.

Strong indirect evidence in support of our ACO2 hypothesis is derived from the bacteriology literature. Microbial iron chelators have been studied for years as candidate drugs for the treatment of hemosiderosis. When iron is deficient, bacteria use citrate to synthesize highly-specific iron chelators; they simultaneously synthesize membrane receptors which recognize the iron chelator complex (56). Parenthetically, we note that citrate itself is an important intracellular iron chelator in all cells. During development, bacteria express at least two isoforms of aconitase; each isoform is associated with a different rate of iron uptake by the organism (57). Moreover, man-made bacterial mutants which cannot grow on iron deficient medium (i.e. cannot make iron chelators from citrate, see 58, 59), cannot grow at all on citrate and thus appear to be aconitase mutants; they are also resistant to manganese (Mn) toxicity (56). In short, both citrate and aconitase play critical roles in microbial iron and energy metabolism. In light of our evidence for an altered form of ACO2 in IPD, and the location of the ACO2 gene on chromosome 22q13, we feel that the ACO2 "isoform" hypothesis deserves considerable attention.

Finally, manganese (Mn), which induces levodopa-responsive parkinsonism (9, 10), is a potent inhibitor of ACO2. Previous investigators have demonstrated that Mn can occupy the fourth Fe site (i.e. the citrate binding site) in the enzyme active site (FIG. 2, Part C) (60). Using commerically available purified pig aconitase, we have recently observed that Mn alters aconitase Km but not Vmax. Thus, one may reasonably conduct experiments to determine whether patients with IPD have altered "endogenous" ACO2 kinetics; such altered kinetics could contribute to altered mitochondrial energy and iron metabolism.

It is unclear how iron is regulated in mitochondria, but both ATP and citrate appear to play a role (61). We propose that ACO2 plays a role in mitochondria similar to the role ACO1 plays in the cytosol. In our model, an altered ACO2 would be more often in the open configuration, where it loses aconitase activity and acts as an mRNA binding protein (FIG. 2, Part B). ACO2 would bind to mitochondrial DNA encoded mRNAs, thus altering protein synthesis. As a result, decreased levels of Complex I would occur, which is a known manifestation of IPD (32–35). At the same time, progression through the citric acid cycle would be decreased due to slightly reduced aconitase activity (FIG. 1), altering cellular metabolism. The altered form of ACO2 would lead to increased synthesis of a not-yet-identified mitochondrial membrane equivalent of the cell membrane transferrin receptor; such receptor would increase iron uptake into mitochondria, ultimately leading to free radical generation and cell death. In support of this hypothesis are these four points: 1) ACO2 has a 4Fe-4S cubane cluster; 2) there appears to be a defect in mitochondria in IPD; 3) there are increased iron levels in substantia nigra in IPD; and 4) there may be isoforms of ACO2 specific to brain (see below) with potentially different activities.

SUMMARY OF THE INVENTION

This invention provides methods of determining the susceptibility to Parkinson's disease of a subject and of diagnosing Parkinson's disease in a subject which comprises detecting in a sample from the subject the presence of a composition of matter, which composition comprises a band having an apparent molecular weight of about 83 kilodaltons as determined by denaturing polyacrylamide gel electrophoresis, is capable of being specifically detected by an antibody directed to mitochondrial aconitase hydroxylase, and has greater electrophoretic mobility than the corresponding unaltered composition as determined by non-denaturing polyacrylamide gel electrophoresis.

BRIEF DESCRIPTION OF THE FIGURES

FIG. 6. Association between markers on chromosome 22q13 and Parkinson's disease. Statistical significance values for $p<0.05$, $p<0.01$, and $p<0.001$ are illustrated by arrows. The p values correspond to the log likelihood ratio $\chi^2$. The asterisk indicates the $\log(1/p)$ for a multivariate model ($p<0.0011$). All markers shown are within 10 kilobase of each other on chromosome 22. The interleukin-2 receptor β gene (IL2RB) and the platelet-derived growth factor β gene (PDGFβ) are among the markers shown.

FIG. 7. Lineweaver-Burke plot of ACO2 reaction kinetics determined as described in the text. Aconitase activity is expressed as nanomoles of product per milligram of protein per minute.

FIG. 8. ACO2 gene cDNA sequence and predicted amino acid sequence.

FIG. 9. Oligonucleotide primers used to amplify ACO2 gene exons.

FIG. 10. ACO2 gene exon and intron data.

DETAILED DESCRIPTION OF THE INVENTION

Definitions

Figure 1:
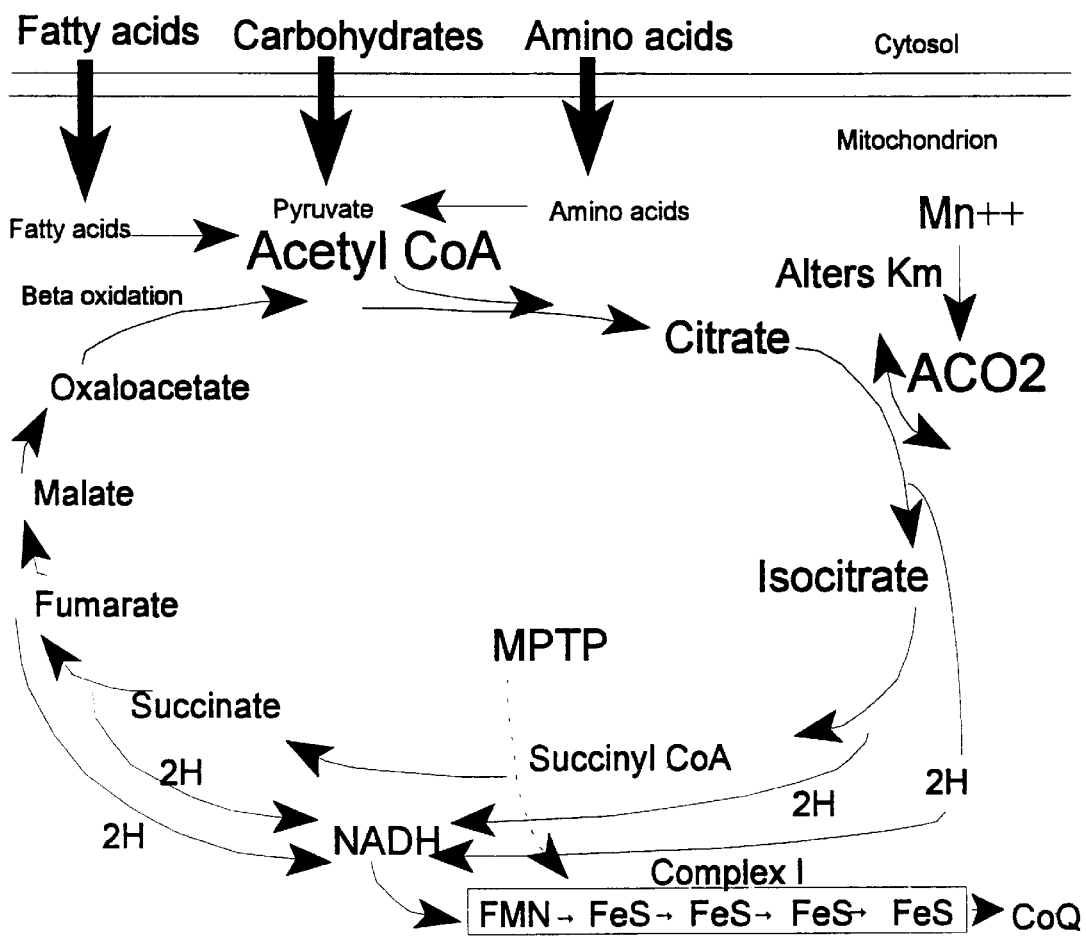
FIG. 1. The citric acid cycle. Mitochondrial aconitase hydroxylase (ACO2) is depicted at right catalyzing the interconversion of citrate and isocitrate. MPTP is N-methyl-4-phenyl-1,2,3,6-tetrahydropyridine.
Figure 2:
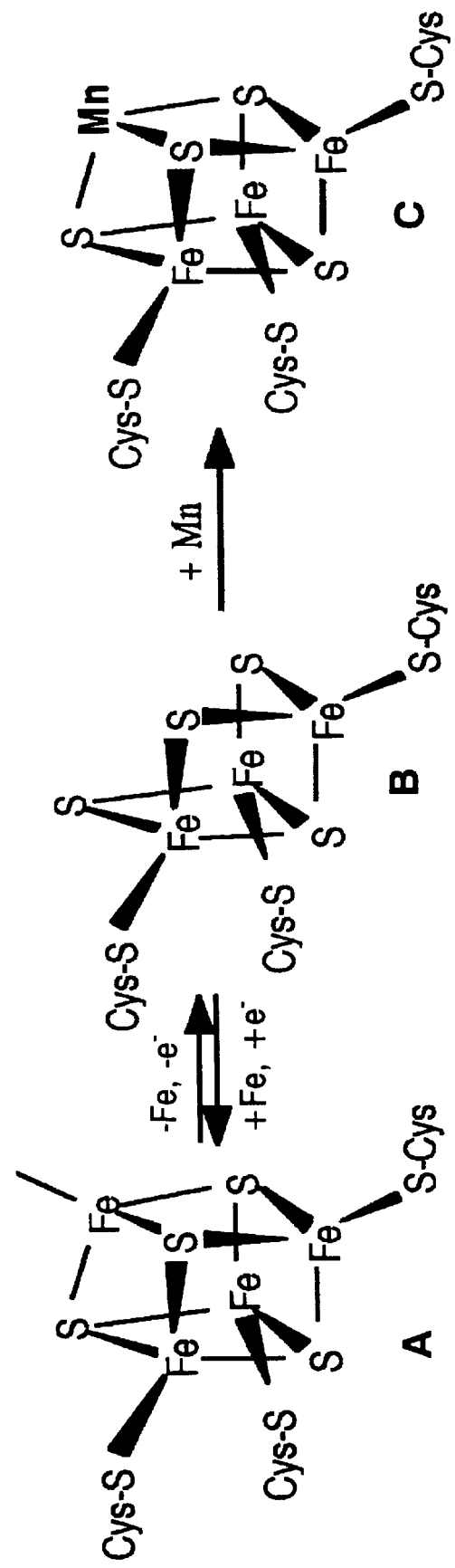
FIG. 2. Cubane citrate binding site of ACO2 and ACO1. Part A. The 4Fe-4S enzymatically-active site of aconitase (see reference 69). Part B. The 3Fe-4S mRNA-binding form of aconitase (see reference 27). Part C. The manganese ($Mn^{++}$)-inhibited form of aconitase which has altered enzyme kinetics (see reference 60).

As used herein, the phrases "isoform" and "altered form" are synonymous. When referring to mitochondrial aconitase hydroxylase (ACO2), such isoform or altered form includes any ACO2 derived from genetic mutation, alternative mRNA splicing or post-translational modification. Further, such isoform or altered form includes any ACO2 derived from a non-covalent modification, such as a change in ACO2 conformation (molecular shape) or binding to another identified or unidentified protein or other substance. For example, an isoform or altered form which is manifest on a non-denaturing gel or an isoelectric focusing gel, whether detected by anti-ACO2 antibody (Western blot staining) or by aconitase enzyme activity (activity staining), may arise from any of the mechanisms listed above or from any combination of them.

The phrase "purified" or "isolated" when referring to a protein, means a chemical composition which is essentially free of other cellular components. Purity and homogeneity are typically determined using analytical techniques such as polyacrylamide gel electrophoresis or high performance liquid chromatography. A protein which is the predominant species present in a preparation is purified. Generally, a purified or isolated protein will comprise more than 80% of all macromolecular species present in the preparation. Preferably, the protein is purified to greater than 90% of all macromolecular species present. More preferably, the protein is purified to greater than 95% and most preferably the protein is purified to essential homogeneity, wherein other macromolecular species are not detected by conventional techniques.

The phrase "specifically detected by an antibody" when referring to a protein, refers to a binding reaction which is determinative of the presence of the protein or of an antigen or epitope of interest on the protein in the presence of a heterogeneous population of proteins and other biologics.

The Invention

This invention provides a method of determining the susceptibility to Parkinson's disease of a subject which comprises detecting in a sample from the subject the presence of a composition of matter, which composition comprises a band having an apparent molecular weight of about 83 kilodaltons as determined by denaturing polyacrylamide gel electrophoresis, is capable of being specifically detected by an antibody directed to mitochondrial aconitase hydroxylase, and has greater electrophoretic mobility than the corresponding unaltered composition as determined by non-denaturing polyacrylamide gel electrophoresis.

In one embodiment, the sample is serum. In another embodiment, the serum sample comprises buffy coat or white blood cells.

This invention provides a method of diagnosing Parkinson's disease in a subject which comprises detecting in a sample from the subject the presence of a composition of matter, which composition comprises a band having an apparent molecular weight of about 83 kilodaltons as determined by denaturing polyacrylamide gel electrophoresis, is capable of being specifically detected by an antibody directed to mitochondrial aconitase hydroxylase, and has greater electrophoretic mobility than the corresponding unaltered composition as determined by non-denaturing polyacrylamide gel electrophoresis.

In one embodiment, the sample is serum. In another embodiment, the serum sample comprises buffy coat or white blood cells.

It will be understood that the altered composition of matter detected may include multiple components, at least one of which is present in an altered form specific to IPD. Such components include, but are not limited to, proteins, cofactors which bind thereto, or any other biologic which may account for greater mobility relative to non-IPD controls observed on non-denaturing polyacrylamide gels.

In one embodiment, the altered composition of matter comprises an altered form of a protein. In another embodiment, the protein is human mitochondrial aconitase hydroxylase (ACO2). An altered human ACO2 may arise from a change specific to IPD.

It will be understood that the Parkinson's disease tests of the invention are not per se dependent on the existence of an altered form of ACO2. The molecular nature underlying the greater mobility of the composition of matter detected on non-denaturing polyacrylamide gels in IPD (i.e. the shifted band, see FIG. 3) may comprise an altered form of ACO2. The shifted band may also comprise an unaltered form of ACO2 present in the composition of matter with additional, unidentified component(s) which themselves account for greater mobility.

It will be understood that complete characterization of the molecular components of the composition of matter is not essential for successful use of the Parkinson's disease tests described herein. In simplest form, a complete test comprises detecting the shifted band in the serum of a subject.

Such detection is predictive of susceptibility to IPD or is diagnostic of IPD by virtue of the strong positive correlation between the presence of the shifted band and the presence of IPD described herein.

It will be appreciated that the same test (i.e. presence of the shifted band) may be used for susceptibility or diagnostic testing depending upon the medical history of the subject taking the test. For example, in subjects which do not yet display clinical signs of Parkinson's disease, the test predicts susceptibility. In patients with borderline or inconclusive clinical signs of Parkinson's disease, the test is diagnostic. While susceptibility to Parkinson's disease may be determined solely on the basis of test results, a skilled practitioner will exercise clinical judgment together with the results of the test to determine a diagnosis.

It will be appreciated that when the shifted band is subsequently cut out of a non-denaturing polyacrylamide gel and run on a second, denaturing polyacrylamide gel, a prominent band at 83 kDa is observed. Further, the band at 83 kDa is capable of being specifically detected by an antibody directed to ACO2.

It will further be appreciated that alternative formats of the same test are provided. That is, given the existence of the non-denatured composition of matter specific for IPD, one skilled in the art would know how to design other test formats for it's detection. Such test formats include, but are not limited to, non-denaturing agarose gel electrophoresis, isoelectric focusing and any other type of separation capable of detecting a difference in the shape or charge of a composition of matter. Further, given the existence of the non-denatured composition of matter specific for IPD, one skilled in the art would know how to design an antibody capable of it's detection. Such an antibody might be directed to an altered form of ACO2.

This invention is illustrated by examples set forth in the Experimental Details section which follows. This section is provided to aid in an understanding of the invention but is not intended to, and should not be construed to, limit in any way the invention as set forth in the claims which follow thereafter.

Experimental Details

EXAMPLE 1

Summary. Compared to controls, subjects with idiopathic Parkinson's disease (IPD) have: 1) a perturbation in iron metabolism; 2) a bandshift detectable by non-denaturing electrophoresis which contains the citric acid cycle enzyme known as mitochondrial aconitase hydroxylase (ACO2); 3) an allelic association of two dinucleotide repeat markers on chromosome 22q13, which chromosome includes the ACO2 gene; and 4) increased intake of calories. These observations lead to the general hypothesis that IPD results from a mutation or post-translational modification of ACO2 which, in turn, alters mitochondrial function. Four specific hypotheses and methods to evaluate them are set forth below.

Hypothesis 1. Alterations in systemic iron metabolism and energy metabolism are consistent manifestations of IPD and may worsen with disease progression. To test this hypothesis it is necessary to confirm the previously-observed perturbation of systemic iron metabolism by measuring circulating concentrations of ferritin, iron, total iron binding capacity (TIBC), hemoglobin, transferrin, transferrin receptor (Tfr) and lactoferrin in patients with IPD and controls at two critical disease stages: early (untreated) and late. Further, it is necessary to confirm differences in caloric intake over time between IPD patients and controls.

Hypothesis 2. An altered form (isoform) of the ACO2 protein imparts susceptibility to IPD. This hypothesis may be tested by: (a) using polyclonal or monoclonal antibodies directed to human ACO2 as Western blot reagents to detect biochemical differences in post-mortem brain tissue and in buffy coats of IPD patients and controls; (b) determining if the brain ACO2 isoform of IPD patients is structurally different from that of normal controls; (c) identifying a specific alteration in the ACO2 protein in IPD, localizing the position of the alteration in ACO2 by peptide mapping and isolating and identifying a variant peptide fragment associated with IPD; (d) further determining the specificity of the electrophoretically-shifted serum band for IPD by examining its frequency in a larger group of IPD patients and controls and in patients with essential tremor, Huntington's disease and Alzheimer's disease; and (e) determining the frequency of known ACO2 enzyme isoforms in IPD patients and controls.

Hypothesis 3. Specific mutations in the ACO2 transcription unit, and/or its iron-responsive element, predispose to IPD. This hypothesis may be tested by identifying transcribed sequences and screening DNA from IPD patients and controls for mutations by direct sequencing of ACO2.

Hypothesis 4. The variant form of ACO2 in IPD alters mitochondrial function. This hypothesis may be tested by: (a) assessing the bidirectional enzyme kinetics of ACO2 in IPD patients and controls using buffy coat mitochondria; (b) determining whether or not ACO2 regulates the translation of proteins encoded by the mitochondrial genome (e.g. those of complex I) similar to the way that cytosolic aconitase (ACO1) regulates translation of iron metabolism proteins encoded by the nuclear genome; and (c) correlating the differences in ACO2 protein to possible differences in DNA structure by reverse transcriptase-polymerase chain reaction (RT-PCR).

Tests of Hypotheses

From an epidemiologic point of view, it needs to be determined whether the pertubation in iron metabolism and in caloric intake is a manifestation of IPD that will worsen with disease progression or if it is a change induced by treatment of the disease. Our previous laboratory efforts identified a potential mechanism which might explain the alteration of iron metabolism in IPD and may also clarify the basis for the mitochondrial disorder present in this illness. We need to determine whether or not ACO2 in IPD is altered genetically or biochemically and investigate its function in IPD. Both our previous work and the literature support the hypotheses set forth herein.

Peripheral iron stores and IPD. In IPD brain, iron levels in the substantia nigra are higher than expected and lactoferrin receptors (22) are upregulated relative to controls. In contrast, ferritin concentrations are lower in IPD relative to controls which could accelerate free radical formation and lipid peroxidation. It has not been clear whether this deposition of iron is a primary event that induces oxidative death of substantia nigra neurons, or whether it is simply a consequence of the disease. We tested the hypothesis that systemic iron metabolism may be perturbed in IPD. Because our initial observations were highly intriguing, we expanded the work.

Serum iron and total iron binding capacity (TIBC) were measured by an atomic absorption graphite furnace micromethod (68). Serum ferritin and transferrin receptor concentrations were determined by radioimmunoassay, and transferrin was measured by a commercially available immunodiffusion assay (Ramco Laboratories, Houston). Dietary iron was also assessed. TIBC, transferrin, serum iron and ferritin concentrations were all significantly lower in IPD patients compared with controls. In the face of lower serum iron and ferritin, normally indicative of decreased iron stores, one would expect TIBC, transferrin and transferrin receptors levels to be elevated. Nonetheless, lower concentrations of TIBC and transferrin were observed.

The results were unchanged when IPD cases without dementia were considered separately. Moreover, TIBC and serum iron as dependent variables in a multivariate regression model adjusting for potential confounders were both strongly associated with IPD case status. To our surprise, dietary iron intake was higher in patients with IPD than controls, but the difference disappeared when the overall intake (diet and supplemental use) was considered. Furthermore, neither the total caloric intake nor the total fat intake appeared to be related to these iron storage parameters. These parameters of iron were similar in the 25 patients with IPD who were untreated with levodopa compared to those on levodopa therapy.

The mechanism whereby iron status influences the synthesis of the major proteins of systemic iron metabolism (e.g. ferritin, transferrin receptor and transferrin) has been carefully studied for more than a decade by Klausner (27, 53–55) and others (69). The mRNAs of each of these proteins contain a highly-conserved nucleotide sequence referred to as the iron responsive element (IRE). Translation of the mRNAs of these proteins is largely controlled by a cytosolic protein now known as IRP1, or cytosolic aconitase (ACO1); a second, more poorly studied protein (IRP2) also plays a role (70). The amino acid sequence of IRP1 has 57% homology with ACO2, the citric acid cycle enzyme responsible for the interconversion of citrate and isocitrate.

Both ACO1 and ACO2 have 4Fe-4S cubane clusters in their active (i.e. citrate-binding) sites. When iron is scarce, cytosolic aconitase shifts to an "open" 3Fe-4S configuration and becomes an mRNA IRE-binding-protein which, in turn, decreases the synthesis of ferritin and increases the synthesis of transferrin and transferrin receptor. Because we observed that, in IPD, both serum ferritin and transferrin concentrations were depressed, we initially postulated that cytosolic aconitase (ACO1) might be somehow altered in IPD. We have now obtained compelling systemic and genetic data (discussed below) that ACO2 may be the defective gene. Moreover, we hypothesize that the 3Fe-4S form of ACO2 may—within the mitochondrion—regulate the translation of proteins encoded by the mitochondrial genome, e.g. the membrane-bound ND1–ND6 subunits of Complex I (71).

Figure 3:
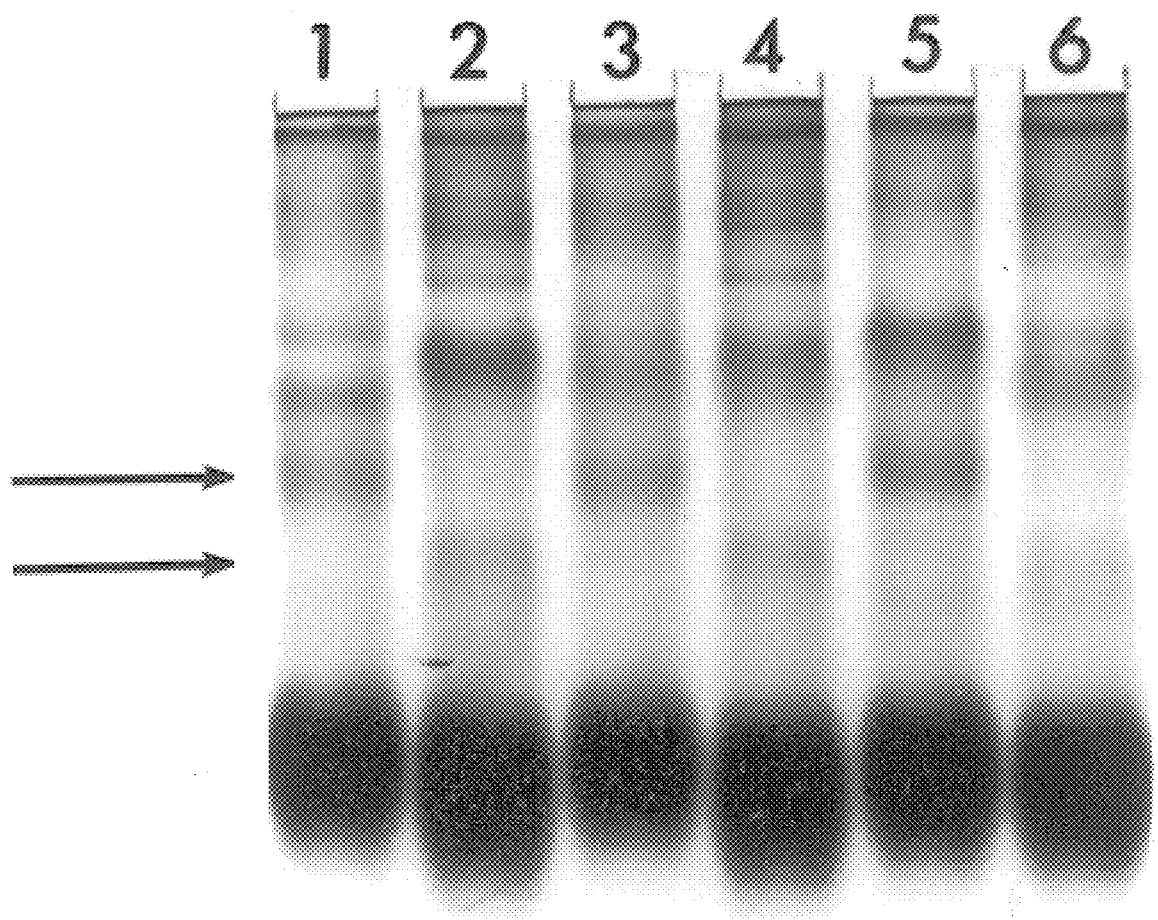
FIG. 3. Neutral (non-denaturing) polyacrylamide gel electrophoresis (PAGE) of serum proteins from controls (lanes 1, 3 and 5) and idiopathic Parkinson's disease (IPD) cases (lanes 2, 4 and 6). The arrows indicate a band which was consistently shifted in 93% of IPD cases. This band-of-interest was subsequently cut out and run on denaturing sodium dodecyl sulfate (SDS) PAGE (see FIG. 4).
Figure 4:
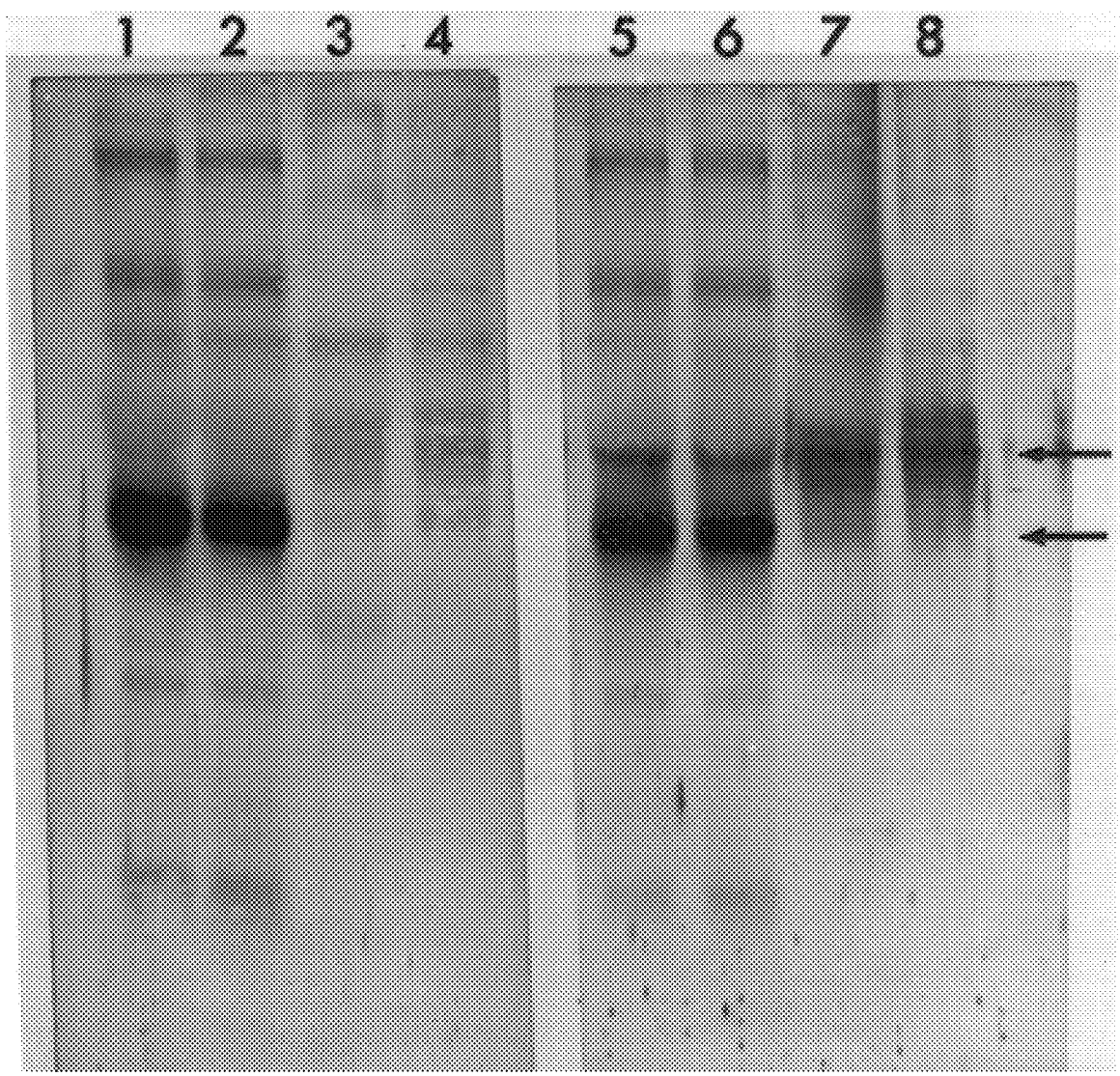
FIG. 4. SDS-PAGE of serum proteins (lanes 1, 2, 5 and 6) and the band-of-interest from FIG. 3 (lanes 3, 4, 7 and 8), stained by Western blot using an antibody directed to bovine ACO2. Lanes 1–4 were probed with preimmune serum and lanes 5–8 were probed with immune serum. Control lanes are the even-numbered lanes. IPD lanes are the odd-numbered lanes. In lanes 1, 2, 5 and 6, the major dark 66 kilodalton (kDa) band (lower arrow) was albumin. In lanes 3, 4, 7 and 8, a band at 83 kDa (upper arrow) was specifically detected by an antibody directed to bovine ACO2. The molecular weight of ACO2 is known to be 83 kDa.
Figure 5:
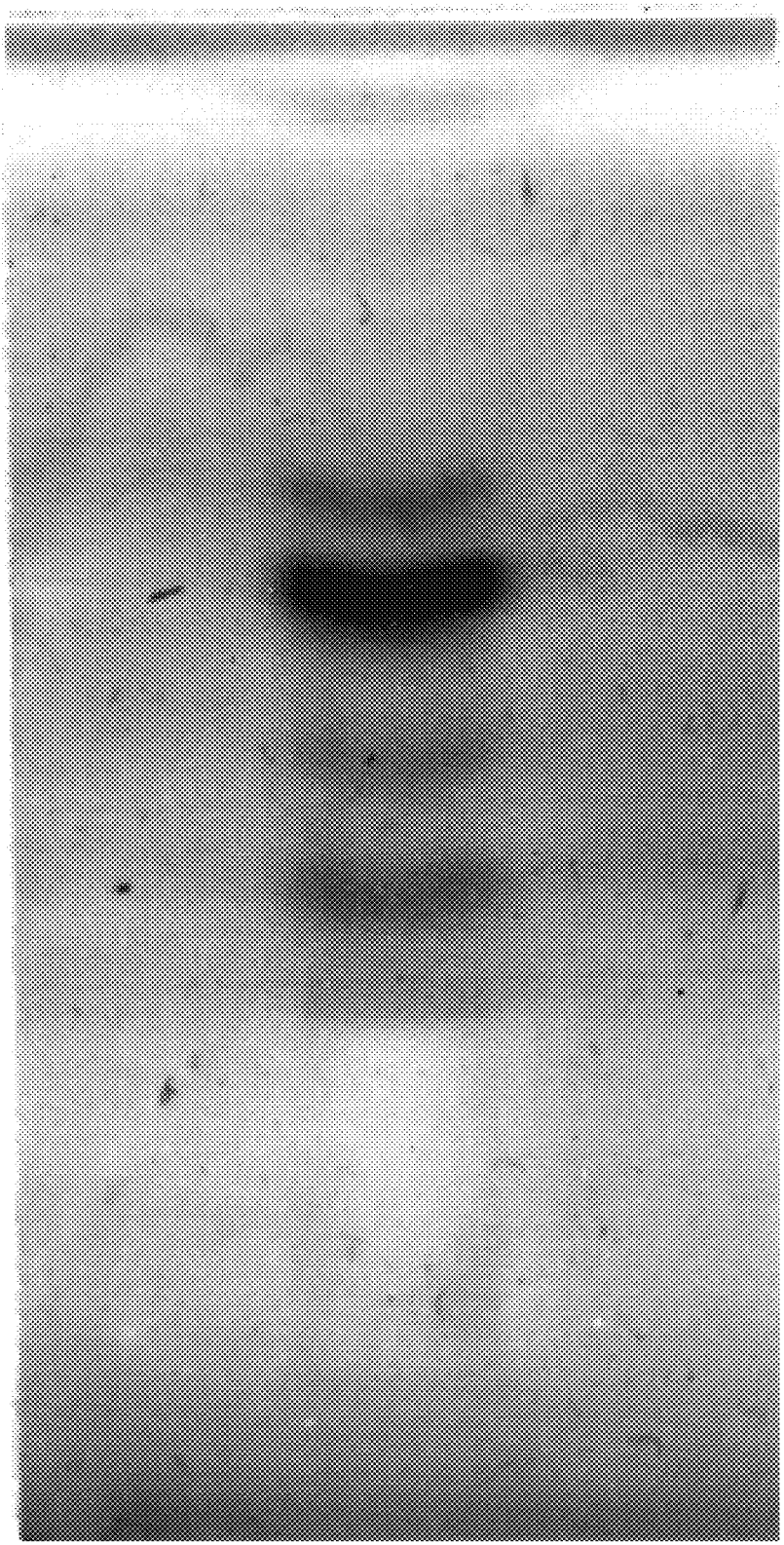
FIG. 5. Isoelectric focusing (IEF) of placental ACO2 performed as described in the text.

The evidence we have derived from separate lines of investigation can be summarized as follows: 1) allelic association with IPD near dinucleotide repeat markers on chromosome 22q13 includes the ACO2 gene; and 2) a consistently-shifted protein-containing band (stained with Coomassie blue) with greater electrophoretic mobility on non-denaturing gels in IPD cases as compared to controls (FIG. 3). When these non-denatured protein-containing bands of cases and controls were cut out and run on denaturing sodium dodecyl sulfate (SDS) gels, both proved to contain some albumin plus a major protein at approximately 83 kilodaltons, i.e. the known molecular weight of ACO2. Using an antibody directed to bovine ACO2, we have identified the 83 kDa protein as ACO2 (FIG. 4). Thus, we infer that there may be a mutation in the ACO2 gene itself, a splicing variant, or a post-translational protein modification. Because isoforms of ACO2 have been described (28), we have established a method to examine ACO2 in IPD cases and controls using isoelectric focusing (IEF). IEF of fresh human placental mitochondria has yielded two major and two minor bands, stained based on enzyme activity (FIG. 5). These bands presumably correspond to the four ACO2 isoforms described 20 years ago by Slaughter et al (28).

In studying brain ACO2 isoforms from frozen post-mortem tissue, one can use IEF and a staining method based on enzyme activity (28). Preliminary experiments show that brain tissue samples that stain express a single band which differs from the major band of human placenta. Brain ACO2 isoforms have not previously been studied in humans. Using human placenta, one can purify trace quantities of ACO2 using a combination of gel chromatography and HPLC. Purified human placental ACO2 can be used to generate specific polyclonal and monoclonal antibodies. These antibodies may then be used to study brain ACO2 isoforms from banked post-mortem brain tissue of IPD patients and controls.

CYP2D6 Polymorphisms in Patients with IPD and Controls. Because the allelic association of CYP2D6 (on chromosome 22q13) with IPD is inconsistent (5–8), it is possible that there is no causal relationship between the two. Locus-specific amplification of blood DNA was done on IPD patients and controls. The frequency of the CYP2D6 "B" allele was similar in IPD patients and controls (IPD 18.6% versus controls 17.6%). Homozygosity for the "B" allele was also similar (IPD 5% versus controls 3.7%). A single control and no IPD patients had an "A" allele, and no other variant alleles of CYP2D6 were identified.

We compared the allele frequencies in IPD patients and controls in the set of 10 dinucleotide repeat markers in the region near CYP2D6 (FIG. 6). Alleles for adjacent markers, D22S272, D22S284 were different between IPD patients and controls but did not reach the a priori level of statistical significance. The maximum $\log(1/p)$ for D22S272 was 2.5 suggesting a possible association in the region. Using the multivariate log likelihood model chi square, only alleles for markers D22S272 and D22S284 were significantly different among IPD patients and controls. The log likelihood chi square was 13.3, $p<0.001$, maximum $\log(1/p)=2.96$ for the model. This suggested a better approximation of the association in the region spanning both markers D22S272 and D22S284. Markers for these alleles also remained associated after statistical adjustment for ethnic group and age in the multivariate analysis.

We genotyped two additional dinucleotide repeat makers (D22S445 and D22IL2RB) near D22S272 (FIG. 6) to better approximate the region of interest, but allele frequencies for neither marker were different in IPD patients and controls. Though we also found no evidence for an association between CYP2D6 and IPD in this case-control study, we provide an alternative explanation with data suggesting that there may be an unidentified locus for susceptibility to IPD that is in linkage disequilibrium with CYP2D6. The frequency of alleles for 2 nearby dinucleotide repeat markers was different in IPD patients compared with controls.

We appreciate that the use of dinucleotide markers to detect linkage disequilibrium in case-control studies is problematic (72). Linkage is only one of the reasons for detecting allelic association. Nevertheless our results, coupled with the data from earlier studies (5–8), suggest that a locus in the region around CYP2D6 on chromosome 22q13 imparts IPD susceptibility. The implicated region contains more than 1 million base pairs of DNA and would be expected to contain more than 50 genes, most of which have not been identified. Mitochondrial aconitase hydroxylase (ACO2) is in this group and provides one of many reasons to continue to focus efforts towards the localization and positional cloning of the gene responsible for IPD susceptibility on chromosome 22q13.

Detection of a variant form of ACO2. We detected a shifted band using neutral (non-denaturing) polyacrylamide gels and serum of IPD patients compared to controls (FIG. 3). When this shifted band was excised, eluted from the gel and run on a denaturing SDS polyacrylamide gel, bands of approximately 83 kDa and 60 kDa were observed (FIG. 4). The 60 kDa band corresponds to albumin, while the 83 kDa band is of a size consistent with several serum proteins including ACO2. Using a polyclonal antibody made against bovine ACO2, but known to cross-react with human ACO2, we demonstrated that the 83 kDa band contained ACO2 by Western blotting. We and others have demonstrated that human serum contains aconitase activity, presumably from mitochondria lost from erythrocyte precursor cells during hematopoiesis. This data suggested that IPD patients might have a different form of ACO2.

Our effort to further study serum ACO2 has been limited by the fact that it is present in serum in small amounts and may be adherent to albumin, which likely affects its mobility. We therefore sought to isolate ACO2 from purified mitochondria. We isolated total mitochondrial protein from human placenta and brain. Following either isoelectric focusing (IEF) or neutral polyacrylamide gel electrophoresis, ACO2 can be detected using an activity stain. Our results indicate that while placenta contains four bands which express aconitase activity, brain expresses only one. However, it is possible that other minor isoforms exist which simply do not retain sufficient activity to stain. Nevertheless, it is remarkable that the stainable brain isoform, presumably the major brain isoform, is different than the major placental form. These studies provide data suggesting the existence of an alternative form of ACO2 in human brain.

Aconitase Activity and Kinetics in Human White Blood Cells. Aconitase catalyzes the interconversion of citrate and isocitrate via the intermediate cis-aconitate. Thus, the kinetics of this enzyme can be studied in either direction. Other investigators (75), who previously considered ACO2 as a likely candidate protein in IPD, studied brain ACO2 activity (not kinetics) in both directions in a series of 7–10 IPD cases and controls. Although their results were not statistically significant for enzyme assays run in either direction, their data are intriguing in that there was a 33% difference in activity when the assay was run from cis-aconitate to isocitrate. Their enzyme assays were run under optimal conditions, with excess substrate. We hypothesize that an "IPD isoform" of ACO2 may have a subtle alteration of enzyme kinetics (i.e. of Vmax and/or Km) which alters mitochondrial iron and energy metabolism. Accordingly, we have established for the first time an assay of ACO2 kinetics in human white blood cells. Conventional cell fractionation techniques were used to prepare mitochondria from buffy coat of 60 ml of whole blood. Thus far, in several normal volunteers, we have studied the kinetics in one direction (i.e. from citrate to cis-aconitate). An example of the method is illustrated in FIG. 7. In this subject, ACO2 had a Vmax of 4.32 nmol/min and a Km of 2.84. Although we have not yet studied ACO2 kinetics in the opposite direction (i.e. from isocitrate to cis-aconitate), we have shown that neither isocitrate nor citrate interfere with the absorbance of the assay product (cis-aconitate) at a UV wavelength of 240 nm. Thus, in this way it is possible to measure ACO2 kinetics in IPD cases and controls.

ACO2 Sequence. BAC clones have been made and 18 putative exons have been sequenced that are homologous to all of the porcine ACO2 coding sequence. PCR primers have been developed (SEQ ID NOs: 3–38) which amplify each of the 18 exons. We have selected cDNA clones from libraries by homology to the putative human mitochondrial aconitase gene exons.

Specificity of shifted serum band detected on neutral polyacrylamide gels in patients with IPD compared to patients with Alzheimer's disease, essential tremor and controls. Among 30 IPD cases, 28 had a shifted band (sensitivity: 93%). Some IPD cases had only the shifted band (putative homozygote pattern) while other IPD cases had the control band plus the shifted band (putative heterozygote pattern). None of 30 controls, only 1 of 30 patients with Alzheimer's disease and none of 10 patients with essential tremor had the shifted band (specificity: 98%).

Definitions for IPD Cases (Patients) and Controls.

Criteria for IPD Cases. Patients with IPD are defined as follows: 1) age 60 years or older; 2) residence for past 3 years in New York metropolitan area; 3) must fulfill all three categories of research diagnostic criteria as specified in Table 1, with the exception

TABLE 1

Criteria for Parkinson's disease

| Category: | |
|---|---|
| 1. | Bradykinesia. |
| 2. | One of the following:<br>a. rigidity;<br>b. rest tremor; or<br>c. postural instability. |
| 3. | At least three of the following:<br>a. unilateral onset;<br>b. persistent asymmetry of signs or symptoms;<br>c. good response to levodopa (MID-LATE only);<br>d. progressive course; and<br>e. levodopa-induced chorea (MID-LATE only). | that for patients with EARLY disease only 2 of the 5 items under category 3 would be required as they will not have been exposed to levodopa; and 4) must not have evidence suggestive of drug-induced parkinsonism or other conditions associated with extrapyramidal features such as progressive supranuclear palsy, Alzheimer's disease or olivopontocerebellar atrophy. These criteria are based on published and recommended research criteria (78,79).

Criteria for Controls. Controls are defined as follows: 1) age 60 years or older; 2) residence for a least 3 years in the New York metropolitan area; and 3) normal neurological examination and history.

Exclusion criteria for IPD Patients. The exclusion criteria are: 1) unable to speak either English or Spanish; 2) not a resident of the greater New York City area; 3) a major, life threatening, medical illness; 4) evidence of progressive dementia; or 5) a history of stroke, repeated head injuries (more than 2 episodes), encephalitis, current neuroleptic use, sustained remission, severe dementia or MPTP exposure. Patients with a history of failure to respond to adequate doses of levodopa (malabsorption excluded) are not considered IPD; rather, they are classified as "parkinsonism". In patients with EARLY disease the levodopa-based criterion is not used.

Exclusion criteria for Controls. The exclusion criteria are: 1) unable to speak either English or Spanish; 2) not residing in the greater New York City area; 3) a major, life threatening, medical illness; 4) evidence of progressive dementia; or 5) a history of stroke, repeated head injuries (more than 2 episodes), encephalitis, current neuroleptic use, or evidence of dementia.

Autopsy protocol. We have secured autopsy in 25% of patients with IPD who died. This is important to confirm clinical diagnosis, and we have secured 64 such brains. Routinely, we record the date, time of death and time that the autopsy was performed to estimate the delay in fixation or freezing. The brain is split into halves through to the brain stem. The left half is fixed in formalin and used to establish the postmortem diagnosis. The right half of the brain is immediately frozen at −70° C.

Collection of Blood for Iron Storage Parameters and DNA. All IPD patients and controls are asked for permission to obtain approximately 30 ml of blood to collect DNA and conduct studies of iron metabolism. The refusal rate for blood drawing has been <3% in our experience in a large epidemiologic project. The blood collected is apportioned into either serum tubes (for PAGE, IEF, ACO2 Western blot analysis, serum iron, ferritin, TIBC, transferrin and transferrin receptor), heparin tubes (for lactoferrin and hemoglobin), or EDTA vacutainer tubes (for DNA isolation). Upon arrival at the laboratory, the name and identification number of each specimen is recorded according to a unique subject ID number; a data entry form is sent directly to the database to record the delivery. DNA is extracted and stored at −70° C. The laboratory is not informed of the subject's case-control status.

For studies of mitochondrial aconitase enzyme kinetics which utilize buffy coat mitochondria preparations, subsets of 60 patients with EARLY IPD, 60 with MID-LATE and 60 controls are asked to provide an additional 60 ml of heparinized blood. This blood drawing should take place on site and should be scheduled independently, as the laboratory must receive the specimen relatively early in the day to complete the enzyme studies on the same day.

Peripheral Iron Metabolism. Work described herein supports the hypothesis that systemic iron metabolism is perturbed in IPD. One can measure serum ferritin (87), iron and TIBC (68), transferrin (88) and transferrin receptors (89) as described. Because new evidence has arisen implicating an upregulation of nigral lactoferrin receptors in IPD (22), one can also measure circulating concentrations of lactoferrin (90), taking care to do so in anticoagulated blood so as not to induce neutrophil release of lactoferrin. One can measure these parameters in patients with IPD and controls in order to assess changes over time (approximately 3 to 4 years). In addition, one can measure these parameters of iron metabolism with respect to stage of disease and treatment status (EARLY vs. MID-LATE) and can be compared with controls matched by age, gender and ethnic group.

Mitochondrial Aconitase (ACO2). In previous sections we have developed our hypothesis that mitochondrial dysfunction in IPD may due to an altered form of ACO2. While IPD is obviously a brain disease, neutral (non-denaturing) gel electrophoresis has revealed a shifted band in blood serum (FIG. 3). Serum ACO2 is most likely derived from erythrocytes which dispose of their mitochondria during maturation. This implies that blood cells express a variant form of ACO2 in IPD. Pragmatically, one can study mitochondria from two tissues—fresh white blood cells (buffy coat) from living subjects and frozen banked brain specimens from deceased subjects—in an effort to determine whether: a) certain isoform(s) of ACO2 are specific to IPD; and b) the kinetics of ACO2 vary between IPD cases and controls.

Development of an antibody to human ACO2. An antibody to human ACO2 can be developed and used to detect the aconitase protein, independent of enzyme activity. See Harlow and Lane (1988) Antibodies: a laboratory manual, Cold Spring Harbor Laboratory, Cold Spring Harbor, N.Y. One can take at least two approaches: protein purification and recombinant expression. Using the first approach, one can purify ACO2 from human placenta or post-mortem brain. See Scopes (1982) Protein Purification: Principles and Practice, Springer-Verlag, New York. Purification is accomplished by chromatography and purity determined by SDS-PAGE. Once purified, both the native protein and the denatured protein can be injected into rabbits or another suitable host to produce polyclonal antibodies. Under the second approach, the human ACO2 cDNA can be used for expression of recombinant human ACO2 in *E. coli*. For example, the cDNA can be inserted into pUC18 and a six histidine tag sequence inserted in frame at the 3' end to allow for isolation on a Ni column (91). The Ni column purified protein can be used to produce antibodies as above.

Isoelectric Focusing (IEF). We have used isoelectrofocusing and neutral polyacrylamide gel electrophoresis to characterize ACO2 from brain and placenta. Our results demonstrate that placenta ACO2 differs from brain ACO2 by both methods. With an anti-ACO2 antibody, one can also use SDS-PAGE and denaturing isoelectrofocusing methods followed by blotting to nylon or nitrocellulose and probing with labeled antibody (92). Frozen brain, because of the large tissue sample size, has often provided ample ACO2 to allow for staining based on enzyme activity. Using human placental mitochondria, one can reproducibly detect aconitase isoforms by IEF and activity staining. Human placental mitochondria reproducibly yield two major and two minor bands with aconitase activity. An example is shown in FIG. 5.

IEF methods. We utilize a Bio-Rad Model 1000/500 power supply and Model 111 Mini IEF cell. Two $\mu$l of semipurified protein preparation are loaded on 1% agarose gel, 1.5 cm from the cathode; we use four parts of ampholytes with a pH range of 6–8, mixed with one part of pH 3–10. To stabilize ACO2, the agarose gel is equilibrated with 0.028 M citric acid (pH 7.4) before loading. Initial focusing is carried out for 15 min at 100V, followed by 15 min at 200V and 60 min at 450V. A larger and more sophisticated Pharmacia IEF system which maintains constant gel temperature throughout the procedure may also be used.

Identification of differences in control and IPD ACO2 protein and localization of the position of the alteration in IPD ACO2 protein. There are a number of possible ways in which an IPD altered form of ACO2 could exist. These include a direct mutation in the DNA, a post-translational modification or a protein made from an alternatively spliced mRNA. One can first identify the position where the alteration occurs and then determine what the alteration is. To localize the alteration, one and two dimensional peptide mapping is carried out.

Mitochondria are isolated from brain tissue and lysed by sonication (93). ACO2 may then be isolated by immunoaffinity chromatography (94) and its purity checked by SDS-PAGE followed by silver staining. Purified ACO2 is digested with various proteases and the fragments are separated on 15% SDS-PAGE. If necessary, fragments may be separated by 2 D gel electrophoresis (95). Peptides are visualized by silver staining and IPD cases and controls compared. Unique peptide(s) are isolated from preparative gels, Coomassie stained and sequenced. This determines if there is a difference in the primary amino acid sequence due to mutation or alternative splicing. If there is no difference in the primary sequence, experiments can be carried out to determine what post-translational modification has occurred. To this end, purified ACO2 may be treated with glycosylases, phosphatases or other enzymes to remove modifications, followed by peptide mapping. Loss of the altered peptide(s) with such treatment indicates the nature of the modification.

Correlation of differences in ACO2 protein to differences in DNA structure using RT-PCR. If results suggest a difference in DNA sequence, this can be confirmed by sequence analysis of the ACO2 gene. If there is alternative splicing, this can be confirmed by RT-PCR (96). In this method, mRNA is isolated from IPD patient and control cells. Oligonucleotide primers, made to regions correlating with IPD-specific changes in peptide maps or covering the entire mRNA along the ACO2 gene, are used to amplify overlapping fragments. Reverse transcriptase is used to make cDNA for each primer set followed by amplification using the polymerase chain reaction (PCR). PfuI (Stratagene) is used due to its low error rate. Double-stranded cDNAs are cloned and sequenced to identify the presence of alternatively-spliced mRNAs. Differences in IPD case and control DNA can be determined. Comparison with genomic DNA can be performed. If alternative splice products exist, one can next examine the genomic sequence of introns surrounding the alternatively-spliced exons to determine changes that may lead to accumulation of an altered splice form.

Development of methods for detecting an altered form of ACO2 in IPD. One can develop tools for detecting altered ACO2. This can be a monoclonal antibody which specifically recognizes the existence of an altered form. Alternatively, if the difference is altered splicing or gene mutation, primers can be designed for PCR analysis of DNA or mRNA.

Determining the mechanism by which altered ACO2 may cause IPD. Our hypothesis proposes that an altered ACO2 leads to IPD. How might altered ACO2 cause the disease? Our working hypothesis, which fits with much of the current data, is that ACO2 functions as a mitochondrial iron regulator, similar to ACO1 regulation of iron homeostasis outside the mitochondrion. As described earlier, ACO1 has a 4Fe-4S cubane cluster. When iron is insufficient, the sulfur with the lowest association constant loses its Fe, assuming a 3Fe-4S configuration. In this state, ACO1 becomes an mRNA binder. Binding to the mRNA of ferritin (97) blocks its translation, thus reducing its protein levels (98). There are four IREs at the 3' end of transferrin receptor (Tfr) mRNA. IRE-BP binding to this sequence stabilizes the mRNA, increasing its half-life, leading to increased Tfr protein synthesis (99).

It is unknown how iron is regulated in mitochondria. We propose that ACO2 regulates the translation of mitochondrial mRNAs. In our model, an altered ACO2 is more often in the open configuration, where it loses aconitase activity but now acts as an mRNA-binding protein. The putative mitochondrial proteins regulated in this fashion need not themselves be iron proteins. Indeed, none of the complex I proteins encoded in the mitochondrial genome are iron proteins. Nevertheless, such misregulation may lead to increased iron uptake and decreased complex I activity. For example, the ND1–ND6 complex I subunits, which anchor the complex I iron-containing subunits to the mitochondrial membrane, could be misregulated. At the same time, progression through the citric acid cycle would be decreased due to slightly reduced aconitase activity (FIG. 1), thus altering cellular metabolism. Finally, an altered ACO2 could lead to increased synthesis of an unidentified mitochondrial equivalent of the Tfr which would increase iron uptake into mitochondria, leading to increased iron uptake into cells, ultimately producing oxidative damage. To test this hypothesis one first needs to determine if ACO2 acts as an mRNA-binding protein in mitochondria, and then look for evidence that this activity is altered in IPD.

In support of this hypothesis, it is known that ACO2 has a 4Fe-4S cubane center (100). As with ACO1, under conditions of reduced iron, one iron is lost in the core of ACO2 (3Fe-S4) with the concommitant loss of aconitase activity. Tissue-specific isoforms of ACO2 exist with potentially different activities. Interestingly, both ACO2 and another Kreb's cycle enzyme, succinate dehydrogenase, have 5' IREs and are regulated by ACO1 (52). We have done a search of the mitochondrial genome for a homologous sequence to the ferritin and Tfr IRE and no match was found. However, the IRE sequence is a relatively nondescript stem-loop structure (53). Considering the evolutionary diversity of mitochondrial DNA compared with nuclear DNA, one would not predict that there would be strong sequence conservation. One can take multiple approaches to determine if ACO2 can act as an mRNA binding protein.

ACO2 mRNA Binding. We have cloned normal human ACO2 and sequenced the full-length cDNA (SEQ ID NO: 1). Thus, purified or bacterially-expressed ACO2 can be used to determine if ACO2 binds mitochondrial mRNAs. The mRNAs are made by producing a series of plasmid constructs containing appropriate mitochondrial-polypeptide-coding sequences, cloned into Bluescript vector. The plasmids are linearized and a $^{32}$P-labeled runoff RNA produced using the T7 promoter of Bluescript. The $^{32}$P-labeled mitochondrial RNA is then incubated with purified ACO2 or bacterially produced ACO2 and the products separated on polyacrylamide gels followed by autoradiography (101). This modified gel mobility shift assay was used to initially determine that heavy chain ferritin contained an IRE. We predict that only ACO2 in the Fe3-S4 configuration should bind while Fe4-S4 ACO2 will not bind. Using desferrioxamine as a tool, one can make iron-deficient and iron-replete ACO2 and quantitate its binding to $^{32}$P-labeled mRNA, in a manner similar to that used by Klausner and coworkers for ACO1.

One can determine whether ACO2 from total mitochondrial protein binds to mitochondrial mRNA. First, mitochondrial protein from placenta can be isolated (93). Next, mRNA binding can be assayed as above using a substrate which bound to purified ACO2. The bound protein can be identified as ACO2 by simply adding ACO2 antibody to the mRNA-protein mixture, which will bind to the ACO2 bound to mRNA. This product will shift to an even slower-migrating position on the gel, sometimes referred to as a supershift (102).

If ACO2 does not bind mitochondrial mRNAs but rather the mitochondrial mRNAs bind to a protein which is not aconitase, one can determine what this mRNA-binding protein is by chromatographically fractionating total mitochondrial proteins and assaying for binding to a $^{32}$P-labeled mitochondrial mRNA. This approach has been used successfully to isolate DNA binding proteins such as the SP1 transcription factor (103).

mRNA Binding Sequence. To determine the ACO2 mRNA binding sequence in mitochondria, one must first determine which mitochondrial mRNAs bind ACO2 (see above). Assuming that there are multiple mRNAs, one can inspect their sequences to identify common sequence patterns, such as inverted repeats, which would form a stem-loop. Using restriction digests, one can delete various sequences from the plasmids used to produce runoff transcripts to produce truncated mRNAs. When the binding site is lost one will no longer detect a shift in the $^{32}$P-labeled mRNA. In this way, one will localize the mRNA binding site. Alternatively, one can RNase treat the $^{32}$P-labeled mRNA following protein binding and isolate the protected RNA fragment. RNA fingerprinting would reveal the RNA sequence. Ultimately, oligonucleotide-directed mutagenesis can be used to generate point mutations in the putative binding site to determine important sequences in the IRE (104).

Link Between ACO2 and IPD. Our model makes two predictions. First, IPD ACO2 will have increased IRE binding compared to normal ACO2. One can quantitate the binding of purified ACO2 to mitochondrial mRNA using the gel mobility shift assay, comparing IPD case and control ACO2. Second, proteins regulated by ACO2 will be reduced in abundance. Based on our gel mobility shift assay results, one can study the levels of proteins encoded by those mRNAs which bind ACO2. This can be done by quantitative Western blotting.

Enzyme Kinetics. We have established for the first time an assay of ACO2 which utilizes buffy coat mitochondria, prepared by conventional cell fractionation techniques. Lineweaver-Burk plots enable calculation of Vmax and Km of the enzyme. Neither citrate nor isocitrate interferes with the absorbance product (cis-aconitate) at 240 nm.

Aconitase Assay. In order to fully activate aconitase, the mitochondrial preparations can be preincubated with $Fe^{++}$ in a solution containing 40 mM HEPES, 10 mM cysteine and 100–500 μM $Fe^{++}$ at 25° C. for 5 min. An aliquot of preactivated enzyme can then be used for the following activity assay and kinetic study.

For measuring enzyme kinetics, varied concentrations of isocitrate and citrate are used as substrate. The assay solutions consist of 20 mM triethanolamine, various concentrations of citrate or isocitrate, and about 0.25 mg protein in a total volume of one ml. The reaction is activated by adding samples into the assay solution. Immediately after addition of enzyme, the change of absorbance at 240 nm is recorded for 2 min. All samples are run in duplicate. Aconitase activity is expressed as nmol product/mg protein/min. Lineweaver-Burke plots are constructed as in FIG. 7. For reactions run in both directions, one can thus compare the Vmax and Km of the enzyme in IPD and controls.

Neutral Gel Electrophoresis of Serum in IPD and other Movement Disorders. Using anti-ACO2 antibody, one can conduct a study on sera from IPD cases, controls, and patients with other movement disorders. This can be done to determine whether the shifted serum band containing ACO2 (FIG. 3) is specific only to IPD or whether it occurs in other neurologic diseases such as essential tremor, Huntington's disease and Alzheimer's disease. Futhermore, one can use postmortem tissue from IPD and other degenerative disorders for this purpose.

Sequence of ACO2. A mutation or polymorphism in the ACO2 gene may predispose to IPD. Alternative alleles could differ by coding sequence or regulatory element. The observation that there are electrophoretic variants of ACO2 suggests that there may be mutations that change the primary sequence of the protein, either by amino acid substitution or alternative splicing. Another possibly is abnormal persistence of normal early developmental forms of ACO2 in IPD.

Given current understanding of the possible role of ACO2 in IPD, one can screen IPD patients and controls for changes in genomic DNA by direct sequence analysis. One can use the primers described in SEQ ID NOs: 3–38 to amplify genomic DNA, which can then be sequenced directly. One can determine whether any polymorphisms found are in linkage disequilibrium with IPD and are likely to be the source of electrophoretic variants detected in serum ACO2.

Because the ACO2 electrophoretic variants may be due to alternative splicing or persistent early developmental forms of ACO2, one should isolate RNA from postmortem brain of IPD patients and controls and screen for alternative transcripts by Northern blot and RNAse protection assays. Any alternative transcripts found could be due to postmortem effects or may represent epiphenomena. Therefore, it is important to identify the corresponding primary DNA sequences and demonstrate their association with IPD prior to concluding that they cause disease.

EXAMPLE 2

Specificity of shifted band in patients with Parkinson's disease compared to patients with Alzheimer's disease, essential tremor and controls. We have now investigated a total of 45 patients with Parkinson's disease. Thirty-four (75%) have only the shifted band (FIG. 3), possibly representing a homozygote pattern. Eleven (25%) have both the upper band seen in controls plus the shifted band, possibly representing a heterozygote pattern. Thus, all IPD patients tested to date have the shifted serum band. None of 30 controls have the shifted band (homozygote or heterozygote pattern); instead, all 30 controls have just the upper band. However, 1 of 20 patients with essential tremor have the heterozygote pattern and 2 of 40 patients with Alzheimer's disease have the homozygote pattern (specificity 87/90= 96.6%).

Status of shifted band in siblings of patients with Parkinson's disease. We examined serum from 14 siblings (one each from 14 probands) of patients with Parkinson's disease previously identified in our investigation. Nine of the 14 siblings (64%) have the shifted band (2 homozygote and 7 heterozygote pattern). We previously established that 2 of these 9 siblings have Parkinson's disease; both of these individuals have the heterozygote pattern (upper and shifted bands present). The other 7 individuals do not currently have Parkinson's disease. Thus, all Parkinson's disease patients have the shifted band as do more than half of the siblings we have tested. The low frequency of the shifted band in controls and patients with other disorders (3/90=3.3%) supports our hypothesis that ACO2 may be genetically modified in Parkinson's disease.

Isoelectric focusing (IEF) of ACO2. Based on our previous IEF/enzyme-activity staining experiments, human brain (cortex) mitochondria express a single isoform of ACO2 which is different from any of the four isoforms that we identified in human placenta (see Example 1). We have now advanced this work using the Pharmacia IEF system. This system allows: (a) greater separation of very similar isoforms; (b) a larger sample volume; and (c) improved preservation of enzyme activity by maintenance of a cold temperature. We made mitochondrial and cytosolic preparations of banked substantia nigra from four IPD cases and four controls. In examining mitochondrial ACO2 isoforms, only two IPD cases and two controls had sufficient activity for staining. This experiment was conducted in blinded fashion and has led to two exciting new observations:

1. Substantia nigra has multiple ACO2 isoforms, all of which are different from those in placenta; and 2. While nigral mitochondrial samples from controls yielded three bands with aconitase activity, nigral mitochondrial samples from patients with Parkinson's disease yielded four bands.

In other words, mitochondria from substantia nigra of IPD patients express an additional ACO2 isoform detectable by the IEF/activity staining assay.

The cytosolic samples from patients and controls can also be examined with this assay to characterize nigral isoforms of ACO1 (IRP1).

References

1. Payami H, Larsen K, Bernard S, Nutt J. Increased risk of Parkinson's disease in parents and siblings of patients. Ann Neurol 1994; 36: 659–661.

2. Waters C H, Miller C A. Autosomal dominant Lewy body parkinsonism in a four-generation family. Ann Neurol 1994;35:59–64.

3. Johnson W G, Hodge S E, Duvoisin R. Twin studies and the genetics of Parkinson's disease—a reappraisal. Mov Disord 1990;5:187–194.

5. Armstrong M, Daly A K, Cholerton S, Bateman D N, Idle J R. Mutant debrisoquine hydroxylation genes in Parkinson's disease. Lancet 1992;339:1017–1018.

6. Diederich N, Hilger C, Goetz C G, Keipes M, Hentges F, Vieregge P, Metz H. Genetic variability of the CYP2D6 gene is not a risk factor for sporadic Parkinson's disease. Ann Neurol 1996; 40: 463–465.

7. Smith C A, Gough A C, Leigh P N, Summers B A, Harding A E, Maraganore D M, Sturman S G, Schapira A H, Williams A C. Debrisoquine hydroxylase gene polymorphism and susceptibility to Parkinson's disease. Lancet 1992;339: 1375–1377.

8. Kurth M C, Kurth J H. Variant cytochrome P450 CYP2D6 allelic frequencies in Parkinson's disease. Am J Med Genet 1993; 48: 166–168.

9. Pentschew W, Ebner F F, Kovatch R M. Experimental manganese encephalopathy in monkeys. J Neuropathol Exp Neurol 1963; 22:488–499.

10. Mena I, Meurin O, Feunzobda S, Cotzias G C. Chronic manganese poisoning. Clinical picture and manganese turnover. Neurology 1967; 17:128–136.

11. Langston J W, Ballard P, Tetrud J W, Irwin I. Chronic parkinsonism in humans due to a product of meperidine-analog synthesis. Science 1983; 219: 979–980.

12. Lux W, Kurtzke J. Is Parkinson's disease acquired? Neurology 1987; 37:467.

13. Li S C, Schoenberg B S, Wang C C, Cheng X M, Rui D Y, Bolis C L, Schoenberg D G. A prevalence survey of Parkinson's disease and other movement disorders in the People's Republic of China. Arch Neurol 1985;42:655–657.

14. Martyn C N, Osmand C. Parkinson's disease and the environment in early life. J Neuro Sci 1995; 132: 201–206.

15. Seidler A, Hellenbrand W, Robra B P, Vieregge P, Nischan P, Joerg J, Oertel W H, Ulm G, Schneider E. Possible environmental, occupational and other etiologic factors for Parkinson's disease: a case-control study in Germany. Neurology 1996; 46: 1275–1284.

16. Morens D M, Grandinetti A, Reed D, White L R, Ross G W. Cigarette smoking and protection from Parkinson's disease: false association or etiologic clue? Neurology 1995; 45: 1041–1051.

17. Golbe L I, Farrell Tm, Davis P. Case-Control study of early life dietary factors in Parkinson's disease. Arch Neurol 1988; 45:1350–1353

18. Cammack R, Wrigglesworth J M, Baum H. Iron-dependent enzymes in mammalian systems. In: Ponka P, Schulman H M, Woodworth, eds. Iron Transport and Storage. Boca Raton:CRC Press, 1990, pp.17–39.

19. Dexter D T, Wells F R, Lees A J, Agid F, Agid Y, Jenner P, Mardsen C D. Increased nigral iron content and alterations in other metal ions occurring in brain in Parkinson's disease. J Neurochem 1989; 52:1830–1836.

20. Galazka-Freidman J, Bauminger E R, Freidman A, Barcikowska M, Hechel D, Nowik I. Iron in parkinsonian and control substantia nigra-a Mossbauer spectroscopy study. Mov Disorders 1996; 11:8–16.

21. Mann V M, Cooper J M, Daniel S E, Srai K, Jenner P, Marsden C D, Schapira A H. Complex I, iron, and ferritin in Parkinson's disease substantia nigra. Ann Neurol 1994; 36:877–881.

22. Faucheux B A, Nillesse N, Damier P, Spik G, Mouatt-Prigent A, Pierce A, Leveugle B, Kubis N, Hauw J-J, Agid Y. Expression of lactoferrin receptors is increased in the mesencephalon of patients with Parkinson's disease. Proc Natl Acad Sci 1995; 92:9603–9607.

23. Dexter D T, Carayon A, Javoy-Agid F Agid Y, Wells F R, Daniel S E, Lees A J, Jenner P, Mardsen C D. Alterations in the levels of iron, ferritin and other trace metals in Parkinson's disease and other neurodegenerative diseases affecting the basal ganglia. Brain 1991; 114:1953–1975.

24. Connor J. R, Snyder B. S, Arosio P, Loeffler D. A, LeWitt P. A quantitative analysis of isoferritins in select regions of aged, parkinsonian and Alzheimer's diseased brains. J Neurochem 1995; 65:717–724.

25. Dexter D T, Carayon A, Vidailhet M, Ruberg M, Agid F, Agid, Y, Lees A. J, Wells F R, Jenner P, Marsden C D. Decreased Ferritin Levels in Brain in Parkinson's Disease. J Neurochem. 1990; 55:16–20.

27. Klausner R D, Rouault T A. A double life: Cytosolic aconitase as a regulatory RNA binding protein. Mol Cell Biol 1993; 4:1–5.

28. Slaughter C A, Hopkinson D A Harris H. Aconitase polymorphism in man. Ann Hum Genet 1975; 39:193–202.

29. Kim U J, Shizuya H, Kang H L, Choi S S, Garrett C L, Smink L J, Birren B W, Korenberg J R, Dunham I, Simon M I. A bacterial artificial chromosome-based framework contig map of human chromosome 22q. Proc Natl Acad Sci USA 1996; 93: 6297–630.

31. Jafrey S R, Cohen N A, Rouault T A, Klausner R D, Snyder S H. The iron-responsive element binding protein: A target for synaptic actions of nitric oxide. Proc Natl Acad Sci USA 1994; 91:12994–12998.

32. Parker W D, Boyson S J, Parks J K. Abnormalities of the electron transport chain in idiopathic Parkinson's disease. Ann Neurol 1989: 26:719–723.

33. Schapira A, Cooper J M, Dexter D, Clark J B, Jenner P, Mardsen C D. Mitochondrial complex I deficiency in Parkinson's disease. Lancet 1989: 1:1269.

34. Mizuno Y, Ohta S, Tanaka M, Takamiya S, Suzuki K, Sato T, Oya H, Dzawa T and Kagawa Y. Deficiences in Complex I subunits of the respiratory chain in Parkinson's Disease. Biochem Biophys Res Commun 1989; 163, 1450–5.

35. Shoffner J M, Watts R L, Juncos J L, Torroni A, Wallace C D. Mitochondrial oxidative phosphorylation defects in Parkinson's disease. Ann Neurol 1991: 30:332–339.

36. Javitch J A, D'Amato R J, Strittmatter S M, Synder S H. Parkinsonism-inducing neurotoxin MPTP: uptake of the metabolite MPP+ by dopamine neurons explains selective toxicity. Proc Natl Acad Sci 1985; 82:2173–2177.

37. Ramsay R R, Dadgar J, Trevor A, Singer T P. Energy driven uptake of MPP+, by brain mitochondria mediates the neurotoxicity of MPTP. Life Sci 1986; 39:581–588.

38. Nicklas, W J, Vyas I, Heikkla R E. Inhibition of NADH-linked oxidation in brain mitochondria by MPP+, a metabolite of the neurotoxin MPTP. Life Sci 1985; 36:2503–2508.

39. Swerdlow R H, Parks J K, Miller S W, Tuttle J B, Trimmer P A, Sheehan J P, Bennett J P Jr, Davis R E, Parker W D Jr. Origin and functional consequences of the Complex I defect in Parkinson's disease. Ann Neurol 1996; 40:663–671.

40. Clayton D A. Replication and transcription of vertebrate mitochondrial DNA. Ann Rev Cell Biol 1991; 7:453–478.

41. Luft R. The development of mitochondrial medicine. Proc Natl Acad Sci USA 1994; 91: 8731–8738.

42. Wallace DC. Diseases of the mitochondrial DNA. Ann Rev Biochem 1992; 61:1175–1212.

43. Fahn S, Cohen G. The oxidant stress hypothesis in Parkinson's disease: evidence supporting it. Ann Neurol 1992; 32: 804–812.

44. Coyle J T, Puttfarcken P. Oxidative stress, glutamate, and neurodegenerative disorders. Science 1993; 262:689–695.

45. Qureshi G A, Baig S, Bednar I Sodersten P, Forsberg G, Siden A. Increased cerebrospinal fluid concentration of nitrite in Parkinson's disease. Neurorep 1995; 6:1642–1644.

46. Connor J R. Cellular and regional maintenance of iron homeostasis in the brain: normal and diseased states. In: Riederer P, Youdim M B H, eds. Iron in Central Nervous System Disorders. New York:Springer-Verlag Wien, 1993; pp. 1–18.

47. Logroscino G, Marder K, Cote L J, Tang M-X, Mayeux R. Dietary lipids and antioxidants in Parkinson's disease: a population-based, case-control study. Ann Neurol 1996; 39: 89–94.

48. Hellenbrand W, Seidler A, Boeing H. Robra B-P, Vieregge P, Nischan P, Joerg J, Oertel W H, Schneider E, Ulm G. Diet and Parkinson's disease II. A possible role for the past intake of specific nutrients. Neurology 1996; 47; 644–650.

49. Gurr M J, Harwood J L. Lipid biochemistry. New York:Chapman and Hall; 1994:; pp. 64–367.

50. Ames B. Dietary carcinogens and anticarcinogens. Oxygen radicals and degenerative diseases. Science. 1983; 221:1256–1264.

51. Gray N K, Hentze M W. Iron regulatory protein prevents binding of the 43S translation pre-initiation complex to ferritin and eALAS mRNAs. EMBO J 1994; 13:3882–3891.

52. Gray N K, Pantopoulos K, Dandekar T, Ackrell B A C, Hentze M W. Translational regulation of mammalian and Drosophila citric acid cycle enzymes via iron-responsive elements. Proc Natl Acad Sci 1996; 93:4925–4930.

53. Klausner R D, Rouault T A, Harford J B. Regulating the fate of mRNA: The control of cellular iron metabolism. Cell 1993: 72:19–28.

54. Jaffrey S R, Haile D J, Klausner R D, Harford J B. The interaction between the iron-responsive element binding protein and its cognate RNA is highly dependent upon both RNA sequence and structure. Nucl Acids Res 1993; 21(19): 4627–31.

55. Rouault T A, Stout C D, Kaptain S, Harford J B, Klausner R D. Structural relationship between and iron-regulated RNA-binding protein (IRE-BP) and aconitase-:functional implications. Cell 1991 64:881–883.

56. Neilands J B. Parallels in the mode of regulation of iron assimilation in all living species. In: Ponka P, Schulman H M, Woodworth R C, eds. Iron Transport and Storage. Boca Raton:CRC Press, 1990; pp. 41–54.

57. Sharma D, Gopalakrishna Y, Nanawati G C, Gollakota K G. Evidence for the existence of two isozymes of aconitase hydratase and its correlation with $^{59}$Fe uptake in *Bacillus cereus* T. Ind J Biochem Biophys 1975; 12:213–215.

58. Pollack J R, Ames B N, Neilands J B. Iron transport in *Salmonella typhimurium:* mutants blocked in the biosynthesis of enterobactin. J Bacteriol 1970; 104:635–639.

59. Hantke K. Selection procedure for deregulated iron transport mutants(fur) in *Escherichia coli* K12:fur not only affects iron metabolism. Mol Gen Genet 1987; 210:135–139.

60. Villafranca J J, Mildvan A S. The mechanism of aconitase action. III. Detection and properties of enzyme-metal-substrate and enzyme-metal-inhibitor bridge complexes with manganese(II) and iron(II). J Biol Chem 1972: 247:3454–3463.

61. Weaver J, Zhan H, Pollack S. Mitochondria have Fe(III) receptors. Biochem J 1990;265;415–419.

62. Mayeux R, Marder K, Cote L J, Denaro J, Hemenegildo N, Mejia H, Tang M-X, Lantigua R, Wilder D, Gurland B, Hauser A. The frequency of idiopathic Parkinson's disease among middle-aged and elderly Black, Hispanic and White men and women in northern Manhattan 1988 to 1993. Am J Epidemiol 1995; 142: 820–827.

63. Marder K, Leung D, Tang M, Bell K, Dooneief G, Cote L, Stern Y, Mayeux R. Are demented patients with Parkinson's disease accurately reflected in prevalence surveys? A survival analysis. Neurology 1991; 41: 1240–4.

65. Marder K, Tang M-X, Alfaro B, Cote L, Louis E, Groves J, Mayeux R. Risk of Parkinson's disease among first-degree relatives: A community-based study. Neurology. 1996; 47: 155–160.

66. Willett W C, Sampson L, Stampfer M J, Rosner B, Bain C, Witschi J, Hennekens C H, Speizer F E. Reproducibility and validity of a semi-quantitative food frequency questionnaire. Am J Epidemiol. 1985;122:51–65.

67. Hellenbrand W, Seidler A, Boeing H. Robra B-P, Vieregge P, Nischan P. Joerg J, Oertel W H, Schneider E, Ulm G. Diet and Parkinson's disease II. A possible role for the past intake of specific nutrients. Neurology 1996; 47; 644–650.

68. Yeh Y-Y, Zee P. Micromethod for determining total iron-binding capacity by flameless atomic absorption spectrophotometry. Clin Chem 1974; 20: 360–364.

69. Beinert H, Kennedy M C. Aconitase, a two-faced protein: enzyme and regulatory factor. FASEB J 1993; 7:1442–1449.

70. Kim H, Klausner R, Rouault T. Translational repressor activity is equivalent and is quantitatively predicted by in vitro RNA binding for two iron-responsive element binding proteins, IRP1 and IRP2. J Biol Chem 1995; 270: 4983–4986.

71. Walker J E. The NADH:ubiquinone oxidoreductase (complex I) of respiratory chains. Quar Rev Biophys 1992; 25:253–324.

72. Ott J. Analysis of Human Genetic Linkage. Baltimore: Johns Hopkins University Press. 1991, pps 241–242.

73. Tang M-X, Tsai W-Y, Marder K, Mayeux R. Linear rank tests for doubly censored data. Statistics Medicine 1995; 14: 2555–2563.

74. Tang M-X, Maestre G. Tsai W-Y, Liu X-H, Feng L, Chung W-Y, Chun M, Schofield P. Stern Y, Tycko B, Mayeux R. Relative risk of Alzheimer's disease and age-at-onset based on APOE genotypes among elderly African-Americans, Caucasians and Hispanics in New York City. Am J Hum Genetics 1996; 58:554–574.

75. Janetzky B, Hauck S, Youdim M B H, Riederer P, Jellinger K, Pantucek F, Zochling R, Boissl K W, Reichmann H. Unaltered aconitase activity, but decreased complexI activity in substantia nigra pars compacta of patients with Parkinson's disease. Neurosci Let 1994: 169:126–128.

76. Hoehn M M, Yahr M D. Parkinson's onset, progression and mortality. Neurology. 1967;17:419–423.

77. Parkinson Study Group: Datatop: a multicenter controlled clinical trial in early Parkinson's disease. Arch Neurol 1989; 46:1052–1060.

78. Hughes A J, Daniel S E, Kilford L, Lees A J. Accuracy of clinical diagnosis of idiopathic Parkinson's disease: a clinico-pathological study of 100 cases. J Neurol Neurosurg Psychiatry. 1992;55:181–184.

79. Hughes A J, Ben-Shlomo Y, Kilford L, Lees A J. What features improve the accuracy of clinical diagnosis in Parkinson's disease: a clinicopathologic study. Neurology 1992;1142–1146.

80. Lohman T G, Roche A F, Martorell R. Anthropometric Standardization Reference Manual. Champaign, Ill.: Human Kinetics Books.

81. Stern M B. The clinical characteristics of Parkinson's disease and parkinsonian syndromes: diagnosis and assessment. In: Stern M B, Hurtig H I, eds. The Comprehensive Management of Parkinson's Disease. New York: PMA Publishing Corp., 1978; pp. 34–39.

82. Schwab J F, England A C. Projection technique for evaluating surgery in Parkinson's disease. In: Billingham F H, Donaldson M C, eds. Third Symposium on Parkinson's disease. Edinburgh: Livingstone, 1969; pp. 152–157.

83. Richards M, Marder K, Cote L, Mayeux R. Interrater reliability and factor structure of the Unified Parkinson's Disease Rating Scale Motor Examination. Mov Disord 1994;9:89–91.

84. Willett W. Nutritional Epidemiology. New York: City Oxford University Press; 1990:127–132.

85. US Department of Agriculture: Agricultural Handbook n. 8 series. Composition of food-raw, processed and prepared. Washington, D.C. US Govt Print Off, 1963–1988.

86. Munger R G, Folsom A R, Kushi L H, Kaye S A, Sellers T A. Dietary assessment of older Iowa women with a food frequency questionnaire: nutrient intake, reproducibility and comparison with 24-hour dietary recall interviews. Am J Epidemiol 1992: 136: 192–200.

87. Miles L, Lipschitz D, Bieter C P, Cook J D. Measurement of serum ferritin by a 2-site immunoradiometric assay. Anal Chem 1974; 61:209–224.

88. The Binding Site. Human transferrin radial immunodiffusion kit. Prod Code No. RN070.3, RA070, 1995.

89. Ramco Laboratories. An enzyme immunoassay for quantifying human transferrin receptors in serum or plasma. Cat No. TF-94, 1995.

90. R&D Systems. Immunoassay of human lactoferrin by the Lacto f-EIA Method. 1995.

91. Smith M C, Furman T C, Ingolia T D, Pidgeon C. Chelating peptide-immobilized metal ion affinity chromatography. A new concept in affinity chromatography for recombinant proteins. J Biol Chem 1988; 263:7211–7215.

92. Burnette W N. "Western blotting": Electrophoretic transfer of proteins from sodium dodecyl sulfate-polyacrylamide gels to unmodified nitrocellulose and radiographic detection with antibody and radioiodinated protein A. Anal Biochem 1981; 112:195–203.

93. Kennedy M C, Emptage M H, Dreyer J-L, Beinert H. The role of iron in the activation-inactivation of aconitase. J Biol Chem 1983; 258 (18):11098–11105.

94. Jack G W. Immunoaffinity chromatography. Mol Biotech 1994; 1:59–86.

95. Hochstrasser D F, Harrington M G, Hochstrasser A C, Miller M J, Merril C R. Methods for increasing the resolution of two-dimensional protein electrophoresis. Anal Biochem 1988; 173:424–435.

96. Lee M S, LeMaistre A, Kantarjian H M, Talpaz M, Freireich E J, Trujillo J M, Stass S A. Detection of two alternative bcr/abl mRNA junctions and minimal residual disease in Philadelphia chromosome positive chronic myelogenous leukemia by polymerase chain reaction. Blood 1989; 73:2165–2170.

97. Caughman S W, Hentze M W, Rouault T A, Harford J B, Klausner R D. The iron-responsive element is the single element responsible for iron-dependent translational regulation of ferritin biosynthesis. Evidence for function as the binding site for a translational repressor. J Biol Chem 1988; 263 (35):19048–19052.

98. Walden W E, Daniels-McQueen S, Brown P H, Gaffield L, Russell D A, Bielser D, Bailey L C, Thach R E. Translational repression in eukaryotes: partial purification and characterization of a repressor of ferritin mRNA translation. Proc Natl Acad Sci 1988; 85:9503–9507.

99. Casey J L, Koeller D M, Ramin V C, Klausner R D, Harford J B. Iron regulation of transferrin receptor mRNA levels requires iron-responsive elements and a rapid turnover determinant in the 3' untranslated region of the mRNA. EMBO J 1989; 8:3693–3699.

100. Surerus K K, Kennedy M C, Beinert H, Munck E. Mossbauer study of the inactive Fe3S4 and Fe3Se4 and the active Fe4Se4 forms of beef heart aconitase. Proc Natl Acad Sci 1989; 86:9846–9850.

101. Leibold E A, Munro H N. Cytoplasmic protein binds in vitro to a highly conserved sequence in the 5' untranslated region of ferritin heavy- and light-subunit mRNAs. Proc Natl Acad Sci USA 1988; 85:2171–2175.

102. Leggett R W, Armstrong S A, Barry D, Mueller C R. Sp1 is phosphorylated and its DNA binding activity down-regulated upon terminal differentiation of the liver. J Biol Chem 1995; 270 (43):25879–25884.

103. Dynan W S, Tijan R. The promoter-specific transcription factor Sp1 binds upstream sequences in the SV40 early promoter. Cell 1983; 35:79–87.

104. Horowitz J A, Harford J B. The secondary structure of the regulatory region of the transferrin receptor mRNA deduced by enzymatic cleavage. New Biol 1992; 4:330–338.

105. Fleiss J L. Statistical Methods for Rates and Proportions. New York: John Wiley and Sons, 1981.

106. Kleinbaum D G, Kupper L L, Muller K E. Applied Regression Analysis and Other Multivariate Methods. Boston: PWS-Kent, 1988, pps. 341–386.

107. Hosmer D W, Lemeshow S. Applied Logistic Regression. New York: John Wiley and Sons, 1989.

108. Willett W, Stampfer M J. Total energy intake implications for epidemiologic analyses. Am J Epidemiol. 1986;124:17–27.

109. Weir B S. Genetic Data Analysis II. Sunderland, Massachusetts: Sinauer Associates, Inc. 1996.

110. Zeger S L, Liang K Y. The analysis of discrete and contiuous longitudinal data. Biometrics 1986; 42: 121–130.

What is claimed is:

1. A method of determining the susceptibility to Parkinson's disease of a subject which comprises detecting in a sample from the subject the presence of a composition of matter, which composition comprises a band having an apparent molecular weight of about 83 kilodaltons as determined by denaturing polyacrylamide gel electrophoresis, is capable of being specifically detected by an antibody directed to mitochondrial aconitase hydroxylase, and has greater electrophoretic mobility as determined by non-denaturing polyacrylamide gel electrophoresis compared with that determined by denaturing polyacrylamide gel electrophoresis, the presence of such a composition of matter in the sample from the subject, indicating susceptibility to Parkinson's disease of the subject.

2. The method of claim 1, wherein the sample is serum.

3. The method of claim 2, wherein the serum sample comprises buffy coat or white blood cells.

4. A method of diagnosing Parkinson's disease in a subject which comprises detecting in a sample from the subject the presence of a composition of matter, which composition comprises a band having an apparent molecular weight of about 83 kilodaltons as determined by denaturing polyacrylamide gel electrophoresis, is capable of being specifically detected by an antibody directed to mitochondrial aconitase hydroxylase, and has greater electrophoretic mobility as determined by non-denaturing polyacrylamide gel electrophoresis compared with that determined by denaturing polyacrylamide gel electrophorese, the presence of such a composition of matter in the sample from the subject, indicating susceptibility to Parkinson's disease of the subject.

5. The method of claim 4, wherein the sample is serum.

6. The method of claim 5, wherein the serum sample comprises buffy coat or white blood cells.

* * * * *

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
       (A) LENGTH: 2580 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: CDS
       (B) LOCATION: 42..2384

(xi) SEQUENCE DESCRIPTION: SEQ ID NO:1:

```
ACGGCAGCAA GGACAGCATC ACATCTTTGT CAGTGCACAA A ATG GCG CCC TAC           53
                                              Met Ala Pro Tyr
                                               1

AGC CTA CTG GTG ACT CGG CTG CAG AAA GCT CTG GGT GTG CGG CAG TAC        101
Ser Leu Leu Val Thr Arg Leu Gln Lys Ala Leu Gly Val Arg Gln Tyr
  5              10                  15                  20

CAT GTG GCC TCA GTC CTG TGC CAA CGG GCC AAG GTG GCG ATG AGC CAT        149
His Val Ala Ser Val Leu Cys Gln Arg Ala Lys Val Ala Met Ser His
                  25                  30                  35

TTT GAG CCC AAC GAG TAC ATC CAT TAT GAC CTG CTA GAG AAG AAC ATT        197
Phe Glu Pro Asn Glu Tyr Ile His Tyr Asp Leu Leu Glu Lys Asn Ile
         40                  45                  50

AAC ATT GTT CGC AAA CGA CTG AAC CGG CCG CTG ACA CTC TCG GAG AAG        245
Asn Ile Val Arg Lys Arg Leu Asn Arg Pro Leu Thr Leu Ser Glu Lys
             55                  60                  65

ATT GTG TAT GGA CAC CTG GAT GAC CCC GCC AGC CAG GAA ATT GAG CGA        293
Ile Val Tyr Gly His Leu Asp Asp Pro Ala Ser Gln Glu Ile Glu Arg
 70                  75                  80

GGC AAG TCG TAC CTG CGG CTG CGG CCG GAC CGT GTG GCC ATG CAG GAT        341
Gly Lys Ser Tyr Leu Arg Leu Arg Pro Asp Arg Val Ala Met Gln Asp
 85                  90                  95                 100

GCG ACG GCC CAG ATG GCC ATG CTC CAG TTC ATC AGC AGC GGG CTG TCC        389
Ala Thr Ala Gln Met Ala Met Leu Gln Phe Ile Ser Ser Gly Leu Ser
                 105                 110                 115

AAG GTG GCT GTG CCA TCC ACC ATC CAC TGT GAC CAT CTG ATT GAA GCC        437
Lys Val Ala Val Pro Ser Thr Ile His Cys Asp His Leu Ile Glu Ala
                 120                 125                 130

CAG GTT GGG GGC GAG AAA GAC CTG CGC CGG GCC AAG GAC ATC AAC CAG        485
Gln Val Gly Gly Glu Lys Asp Leu Arg Arg Ala Lys Asp Ile Asn Gln
                 135                 140                 145

GAA GTT TAT AAT TTC CTG GCA ACT GCA GGT GCC AAA TAT GGC GTG GGC        533
Glu Val Tyr Asn Phe Leu Ala Thr Ala Gly Ala Lys Tyr Gly Val Gly
 150                 155                 160

TTC TGG AAG CCT GGA TCT GGA ATC ATT CAC CAG ATT ATT CTG GAA AAC        581
Phe Trp Lys Pro Gly Ser Gly Ile Ile His Gln Ile Ile Leu Glu Asn
 165                 170                 175                 180

TAT GCG TAC CCT GGT GTT CTT CTG ATT GGC ACT GAC TCC CAC ACC CCC        629
Tyr Ala Tyr Pro Gly Val Leu Leu Ile Gly Thr Asp Ser His Thr Pro
                 185                 190                 195

AAT GGT GGC GGC CTT GGG GGC ATC TGC ATT GGA GTT GGG GGT GCC GAT        677
Asn Gly Gly Gly Leu Gly Gly Ile Cys Ile Gly Val Gly Gly Ala Asp
                 200                 205                 210
```

-continued

| | | |
|---|---|---|
| GCT GTG GAT GTC ATG GCT GGG ATC CCC TGG GAG CTG AAG TGC CCC AAG<br>Ala Val Asp Val Met Ala Gly Ile Pro Trp Glu Leu Lys Cys Pro Lys<br>215                         220                     225 | 725 |
| GTG ATT GGC GTG AAG CTG ACG GGC TCC CTC TCC GGT TGG TCC TCA CCC<br>Val Ile Gly Val Lys Leu Thr Gly Ser Leu Ser Gly Trp Ser Ser Pro<br>230                       235                       240 | 773 |
| AAA GAT GTG ATC CTG AAG GTG GCA GGC ATC CTC ACG GTG AAA GGT GGC<br>Lys Asp Val Ile Leu Lys Val Ala Gly Ile Leu Thr Val Lys Gly Gly<br>245                     250                     255                 260 | 821 |
| ACA GGT GCA ATC GTG GAA TAC CAC GGG CCT GGT GTA GAC TCC ATC TCC<br>Thr Gly Ala Ile Val Glu Tyr His Gly Pro Gly Val Asp Ser Ile Ser<br>                   265                     270                     275 | 869 |
| TGC ACT GGC ATG GCG ACA ATC TGC AAC ATG GGT GCA GAA ATT GGG GCC<br>Cys Thr Gly Met Ala Thr Ile Cys Asn Met Gly Ala Glu Ile Gly Ala<br>             280                       285                     290 | 917 |
| ACC ACT TCC GTG TTC CCT TAC AAC CAC AGG ATG AAG AAG TAC CTG AGC<br>Thr Thr Ser Val Phe Pro Tyr Asn His Arg Met Lys Lys Tyr Leu Ser<br>           295                     300 | 965 |
| AAG ACC GGC CGG GAA GAC ATT GCC AAT CTA GCT GAT GAA TTC AAG GAT<br>Lys Thr Gly Arg Glu Asp Ile Ala Asn Leu Ala Asp Glu Phe Lys Asp<br>310                         315                     320 | 1013 |
| CAC TTG GTG CCT GAC CCT GGC TGC CAT TAT GAC CAA CTA ATT GAA ATT<br>His Leu Val Pro Asp Pro Gly Cys His Tyr Asp Gln Leu Ile Glu Ile<br>325                         330                     335                 340 | 1061 |
| AAC CTC AGT GAG CTG AAG CCA CAC ATC AAT GGG CCC TTC ACC CCT GAC<br>Asn Leu Ser Glu Leu Lys Pro His Ile Asn Gly Pro Phe Thr Pro Asp<br>                   345                     350                     355 | 1109 |
| CTG GCT CAC CCT GTG GCA GAA GTG GGC AAG GTG GCA GAG AAG GAA GGA<br>Leu Ala His Pro Val Ala Glu Val Gly Lys Val Ala Glu Lys Glu Gly<br>             360                       365                     370 | 1157 |
| TGG CCT CTG GAC ATC CGA GTG GGT CTA ATT GGT AGC TGC ACC AAT TCA<br>Trp Pro Leu Asp Ile Arg Val Gly Leu Ile Gly Ser Cys Thr Asn Ser<br>         375                     380                     385 | 1205 |
| AGC TAT GAA GAT ATG GGG CGC TCA GCA GCT GTG GCC AAG CAG GCA CTG<br>Ser Tyr Glu Asp Met Gly Arg Ser Ala Ala Val Ala Lys Gln Ala Leu<br>         390                     395                     400 | 1253 |
| GCC CAT GGC TTC AAG TGC AAG TCC CAG TTC ACC ATC ACT CCA GGT TCC<br>Ala His Gly Phe Lys Cys Lys Ser Gln Phe Thr Ile Thr Pro Gly Ser<br>405                       410                     415                 420 | 1301 |
| GAG CAG ATC CGC GCC ACC ATT GAG CGG GAC GGC TAT GCA CAG ATC TTG<br>Glu Gln Ile Arg Ala Thr Ile Glu Arg Asp Gly Tyr Ala Gln Ile Leu<br>             425                     430                     435 | 1349 |
| AGG GAT CTG GGT GGC ATT GTC CTG GCC AAT GCT TGT GGC CCC TGC ATT<br>Arg Asp Leu Gly Gly Ile Val Leu Ala Asn Ala Cys Gly Pro Cys Ile<br>             440                     445                     450 | 1397 |
| GGC CAG TGG GAC AGG AAG GAC ATC AAG AAG GGG GAG AAG AAC ACA ATC<br>Gly Gln Trp Asp Arg Lys Asp Ile Lys Lys Gly Glu Lys Asn Thr Ile<br>         455                     460                     465 | 1445 |
| GTC ACC TCC TAC AAC AGG AAC TTC ACG GGC CGC AAC GAC GCA AAC CCC<br>Val Thr Ser Tyr Asn Arg Asn Phe Thr Gly Arg Asn Asp Ala Asn Pro<br>470                         475                     480 | 1493 |
| GAG ACC CAT GCC TTT GTC ACG TCC CCA GAG ATT GTC ACA GCC CTG GCC<br>Glu Thr His Ala Phe Val Thr Ser Pro Glu Ile Val Thr Ala Leu Ala<br>485                         490                     495                 500 | 1541 |
| ATT GCG GGA ACC CTC AAG TTC AAC CCA GAG ACC GAC TAC CTG ACG GGC<br>Ile Ala Gly Thr Leu Lys Phe Asn Pro Glu Thr Asp Tyr Leu Thr Gly<br>             505                     510                     515 | 1589 |
| ACG GAT GGC AAG AAG TTC AGG CTG GAG GCT CCG GAT GCA GAT GAG CTT<br>Thr Asp Gly Lys Lys Phe Arg Leu Glu Ala Pro Asp Ala Asp Glu Leu<br>         520                     525                     530 | 1637 |

| | | |
|---|---|---|
| CCC AAA GGG GAG TTT GAC CCA GGG CAG GAC ACC TAC CAG CAC CCA CCC | | 1685 |
| Pro Lys Gly Glu Phe Asp Pro Gly Gln Asp Thr Tyr Gln His Pro Pro | | |
| 535 540 545 | | |
| | | |
| AAG GAC AGC AGC GGG CAG CAT GTG GAC GTG AGC CCC ACC AGC CAG CGC | | 1733 |
| Lys Asp Ser Ser Gly Gln His Val Asp Val Ser Pro Thr Ser Gln Arg | | |
| 550 555 560 | | |
| | | |
| CTG CAG CTC CTG GAG CCT TTT GAC AAG TGG GAT GGC AAG GAC CTG GAG | | 1781 |
| Leu Gln Leu Leu Glu Pro Phe Asp Lys Trp Asp Gly Lys Asp Leu Glu | | |
| 565 570 575 580 | | |
| | | |
| GAC CTG CAG ATC CTC ATC AAG GTC AAA GGG AAG TGT ACC ACT GAC CAC | | 1829 |
| Asp Leu Gln Ile Leu Ile Lys Val Lys Gly Lys Cys Thr Thr Asp His | | |
| 585 590 595 | | |
| | | |
| ATC TCA GCT GCT GGC CCC TGG CTC AAG TTC CGT GGG CAC TTG GAT AAC | | 1877 |
| Ile Ser Ala Ala Gly Pro Trp Leu Lys Phe Arg Gly His Leu Asp Asn | | |
| 600 605 610 | | |
| | | |
| ATC TCC AAC AAC CTG CTC ATT GGT GCC ATC AAC ATT GAA AAC GGC AAG | | 1925 |
| Ile Ser Asn Asn Leu Leu Ile Gly Ala Ile Asn Ile Glu Asn Gly Lys | | |
| 615 620 625 | | |
| | | |
| GCC AAC TCC GTG CGC AAT GCC GTC ACT CAG GAG TTT GGC CCC GTC CCT | | 1973 |
| Ala Asn Ser Val Arg Asn Ala Val Thr Gln Glu Phe Gly Pro Val Pro | | |
| 630 635 640 | | |
| | | |
| GAC ACT GCC CGC TAC TAC AAG AAA CAT GGC ATC AGG TGG GTG GTG ATC | | 2021 |
| Asp Thr Ala Arg Tyr Tyr Lys Lys His Gly Ile Arg Trp Val Val Ile | | |
| 645 650 655 660 | | |
| | | |
| GGA GAC GAG AAC TAC GGC GAG GGC TCG AGC CGG GAG CAT GCA GCT CTG | | 2069 |
| Gly Asp Glu Asn Tyr Gly Glu Gly Ser Ser Arg Glu His Ala Ala Leu | | |
| 665 670 675 | | |
| | | |
| GAG CCT CGC CAC CTT GGG GGC CGG GCC ATC ATC ACC AAG AGC TTT GCC | | 2117 |
| Glu Pro Arg His Leu Gly Gly Arg Ala Ile Ile Thr Lys Ser Phe Ala | | |
| 680 685 690 | | |
| | | |
| AGG ATC CAC GAG ACC AAC CTG AAG AAA CAG GGC CTG CTG CCT CTG ACC | | 2165 |
| Arg Ile His Glu Thr Asn Leu Lys Lys Gln Gly Leu Leu Pro Leu Thr | | |
| 695 700 705 | | |
| | | |
| TTC GCT GAC CCG GCT GAC TAC AAC AAG ATT CAC CCT GTG GAC AAG CTG | | 2213 |
| Phe Ala Asp Pro Ala Asp Tyr Asn Lys Ile His Pro Val Asp Lys Leu | | |
| 710 715 720 | | |
| | | |
| ACC ATT CAG GGC CTG AAG GAC TTC ACC CCT GGC AAG CCC CTG AAG TGC | | 2261 |
| Thr Ile Gln Gly Leu Lys Asp Phe Thr Pro Gly Lys Pro Leu Lys Cys | | |
| 725 730 735 740 | | |
| | | |
| ATC ATC AAG CAC CCC AAC GGG ACC CAG GAG ACC ATC CTC CTG AAC CAC | | 2309 |
| Ile Ile Lys His Pro Asn Gly Thr Gln Glu Thr Ile Leu Leu Asn His | | |
| 745 750 755 | | |
| | | |
| ACC TTC AAC GAG ACG CAG ATT GAG TGG TTC CGC GCT GGC AGT GCC CTC | | 2357 |
| Thr Phe Asn Glu Thr Gln Ile Glu Trp Phe Arg Ala Gly Ser Ala Leu | | |
| 760 765 770 | | |
| | | |
| AAC AGA ATG AAG GAA CTG CAA CAG TGA GGGCAGTGCC TCCCCGCCCC | | 2404 |
| Asn Arg Met Lys Glu Leu Gln Gln * | | |
| 775 780 | | |
| | | |
| CCCCCGCTGG CGTCAAGTTC AGCTCCACGT GTGCCATCAG TGGATCCGAT CCGTCCAGCC | | 2464 |
| ATGGCTTCCT ATTCCAAGAT GGTGTGACCA GACATGCTTC CTGCTCCCCG CTTAGCCCAC | | 2524 |
| GGAGTGACTG TGGTTGTGGT GGGGGGGTTC TTAAAATAAC TTTTTAGCCC CCGTCT | | 2580 |

(2) INFORMATION FOR SEQ ID NO:2:

(i) SEQUENCE CHARACTERISTICS:
        (A) LENGTH: 780 amino acids
        (B) TYPE: amino acid
        (D) TOPOLOGY: linear (ii) MOLECULE TYPE: protein -continued (xi) SEQUENCE DESCRIPTION: SEQ ID NO:2:

Met Ala Pro Tyr Ser Leu Leu Val Thr Arg Leu Gln Lys Ala Leu Gly
 1               5                  10                  15

Val Arg Gln Tyr His Val Ala Ser Val Leu Cys Gln Arg Ala Lys Val
            20                  25                  30

Ala Met Ser His Phe Glu Pro Asn Glu Tyr Ile His Tyr Asp Leu Leu
        35                  40                  45

Glu Lys Asn Ile Asn Ile Val Arg Lys Arg Leu Asn Arg Pro Leu Thr
    50                  55                  60

Leu Ser Glu Lys Ile Val Tyr Gly His Leu Asp Asp Pro Ala Ser Gln
65                  70                  75                  80

Glu Ile Glu Arg Gly Lys Ser Tyr Leu Arg Leu Arg Pro Asp Arg Val
                85                  90                  95

Ala Met Gln Asp Ala Thr Ala Gln Met Ala Met Leu Gln Phe Ile Ser
            100                 105                 110

Ser Gly Leu Ser Lys Val Ala Val Pro Ser Thr Ile His Cys Asp His
        115                 120                 125

Leu Ile Glu Ala Gln Val Gly Gly Glu Lys Asp Leu Arg Arg Ala Lys
    130                 135                 140

Asp Ile Asn Gln Glu Val Tyr Asn Phe Leu Ala Thr Ala Gly Ala Lys
145                 150                 155                 160

Tyr Gly Val Gly Phe Trp Lys Pro Gly Ser Gly Ile Ile His Gln Ile
                165                 170                 175

Ile Leu Glu Asn Tyr Ala Tyr Pro Gly Val Leu Leu Ile Gly Thr Asp
            180                 185                 190

Ser His Thr Pro Asn Gly Gly Gly Leu Gly Gly Ile Cys Ile Gly Val
        195                 200                 205

Gly Gly Ala Asp Ala Val Asp Val Met Ala Gly Ile Pro Trp Glu Leu
    210                 215                 220

Lys Cys Pro Lys Val Ile Gly Val Lys Leu Thr Gly Ser Leu Ser Gly
225                 230                 235                 240

Trp Ser Ser Pro Lys Asp Val Ile Leu Lys Val Ala Gly Ile Leu Thr
                245                 250                 255

Val Lys Gly Gly Thr Gly Ala Ile Val Glu Tyr His Gly Pro Gly Val
            260                 265                 270

Asp Ser Ile Ser Cys Thr Gly Met Ala Thr Ile Cys Asn Met Gly Ala
        275                 280                 285

Glu Ile Gly Ala Thr Thr Ser Val Phe Pro Tyr Asn His Arg Met Lys
    290                 295                 300

Lys Tyr Leu Ser Lys Thr Gly Arg Glu Asp Ile Ala Asn Leu Ala Asp
305                 310                 315                 320

Glu Phe Lys Asp His Leu Val Pro Asp Pro Gly Cys His Tyr Asp Gln
                325                 330                 335

Leu Ile Glu Ile Asn Leu Ser Glu Leu Lys Pro His Ile Asn Gly Pro
            340                 345                 350

Phe Thr Pro Asp Leu Ala His Pro Val Ala Glu Val Gly Lys Val Ala
        355                 360                 365

Glu Lys Glu Gly Trp Pro Leu Asp Ile Arg Val Gly Leu Ile Gly Ser
    370                 375                 380

Cys Thr Asn Ser Ser Tyr Glu Asp Met Gly Arg Ser Ala Ala Val Ala
385                 390                 395                 400

Lys Gln Ala Leu Ala His Gly Phe Lys Cys Lys Ser Gln Phe Thr Ile
                405                 410                 415

```
Thr Pro Gly Ser Glu Gln Ile Arg Ala Thr Ile Glu Arg Asp Gly Tyr
        420                 425                 430

Ala Gln Ile Leu Arg Asp Leu Gly Gly Ile Val Leu Ala Asn Ala Cys
            435                 440                 445

Gly Pro Cys Ile Gly Gln Trp Asp Arg Lys Asp Ile Lys Lys Gly Glu
    450                 455                 460

Lys Asn Thr Ile Val Thr Ser Tyr Asn Arg Asn Phe Thr Gly Arg Asn
465                 470                 475                 480

Asp Ala Asn Pro Glu Thr His Ala Phe Val Thr Ser Pro Glu Ile Val
                485                 490                 495

Thr Ala Leu Ala Ile Ala Gly Thr Leu Lys Phe Asn Pro Glu Thr Asp
            500                 505                 510

Tyr Leu Thr Gly Thr Asp Gly Lys Lys Phe Arg Leu Glu Ala Pro Asp
        515                 520                 525

Ala Asp Glu Leu Pro Lys Gly Glu Phe Asp Pro Gly Gln Asp Thr Tyr
530                 535                 540

Gln His Pro Pro Lys Asp Ser Ser Gly Gln His Val Asp Val Ser Pro
545                 550                 555                 560

Thr Ser Gln Arg Leu Gln Leu Leu Glu Pro Phe Asp Lys Trp Asp Gly
            565                 570                 575

Lys Asp Leu Glu Asp Leu Gln Ile Leu Ile Lys Val Lys Gly Lys Cys
            580                 585                 590

Thr Thr Asp His Ile Ser Ala Ala Gly Pro Trp Leu Lys Phe Arg Gly
        595                 600                 605

His Leu Asp Asn Ile Ser Asn Asn Leu Leu Ile Gly Ala Ile Asn Ile
        610                 615                 620

Glu Asn Gly Lys Ala Asn Ser Val Arg Asn Ala Val Thr Gln Glu Phe
625                 630                 635                 640

Gly Pro Val Pro Asp Thr Ala Arg Tyr Tyr Lys Lys His Gly Ile Arg
                645                 650                 655

Trp Val Val Ile Gly Asp Glu Asn Tyr Gly Glu Gly Ser Ser Arg Glu
                660                 665                 670

His Ala Ala Leu Glu Pro Arg His Leu Gly Gly Arg Ala Ile Ile Thr
            675                 680                 685

Lys Ser Phe Ala Arg Ile His Glu Thr Asn Leu Lys Lys Gln Gly Leu
690                 695                 700

Leu Pro Leu Thr Phe Ala Asp Pro Ala Asp Tyr Asn Lys Ile His Pro
705                 710                 715                 720

Val Asp Lys Leu Thr Ile Gln Gly Leu Lys Asp Phe Thr Pro Gly Lys
            725                 730                 735

Pro Leu Lys Cys Ile Ile Lys His Pro Asn Gly Thr Gln Glu Thr Ile
            740                 745                 750

Leu Leu Asn His Thr Phe Asn Glu Thr Gln Ile Glu Trp Phe Arg Ala
            755                 760                 765

Gly Ser Ala Leu Asn Arg Met Lys Glu Leu Gln Gln
770                 775                 780
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:3:

CTATTTCTGC AAGTGTCTTT GGGC                                                  24

(2) INFORMATION FOR SEQ ID NO:4:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:4:

CCGGGACAGG TACACGAGAA GTTGCA                                                26

(2) INFORMATION FOR SEQ ID NO:5:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:5:

GTCGTGTTCC TTGTGGCTGC TTTGTC                                                26

(2) INFORMATION FOR SEQ ID NO:6:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:6:

TGCCACTATC ACCAAGCATC CTTCAC                                                26

(2) INFORMATION FOR SEQ ID NO:7:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: N (iv) ANTI-SENSE: N

-continued (xi) SEQUENCE DESCRIPTION: SEQ ID NO:7:

AGGTGAGGAG GTGGTGCAGT GAACAG                                            26

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:8:

TGAGCCTCT CGCCCAGTCT TGCCCAC                                            26

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:9:

GGTGGGGAGG GCTTGGTGAG GGTCAC                                            26

(2) INFORMATION FOR SEQ ID NO:10:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:10:

AGAGCATAAG AGCTGATGGA TATGTC                                            26

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:11:

ATTTTTTGGT ATTCTCGGCT GAGGGC                                            26

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:12:

GCTTATTGGT CTCTACCTCC CTCCCA                                      26

(2) INFORMATION FOR SEQ ID NO:13:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:13:

ATCCTGACTT CGTGGCTGGC ACAGGC                                      26

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:14:

AAGGCCACTT CACCGCTTCT ACTCCC                                      26

(2) INFORMATION FOR SEQ ID NO:15:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:15:

TGTGAAGATG CAGGTGGCCG CGTAGC                                      26

(2) INFORMATION FOR SEQ ID NO:16:

(i) SEQUENCE CHARACTERISTICS:

(A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:16:

CTTTCTCAGA GCCTCGGACG CCTGTC                                    26

(2) INFORMATION FOR SEQ ID NO:17:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:17:

TTCACGTGCT CATCCCCGTC CTTGTT                                    26

(2) INFORMATION FOR SEQ ID NO:18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:18:

TGAACTGCTG ACCTCAACTG ACCCAC                                    26

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:19:

AAGAGGCTGT CCCCGCTTCC AAGGTT                                    26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:20:

GTAGGCATAG GTGATTGTCT ACAGCC 26

(2) INFORMATION FOR SEQ ID NO:21:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:21:

TGCTCACTGT CTCCTCCTGA CCCTTA 26

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:22:

ACTCAGCATG GGGTGGGGGA GATGGG 26

(2) INFORMATION FOR SEQ ID NO:23:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:23:

CCACCACATC ACCCCTTCCC ATCAGA 26

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:24:

ACTTCTGGGG CTCTGTACCC TGTG                                   24

(2) INFORMATION FOR SEQ ID NO:25:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:25:

GGAACCCAGC TTATCTGTCC TCGGGA                                 26

(2) INFORMATION FOR SEQ ID NO:26:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:26:

GCTGGGAAGG CCTGTAGCTC CTGGCT                                 26

(2) INFORMATION FOR SEQ ID NO:27:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:27:

CTAGGCTTTT GGTAGGTGCA GGAGAC                                 26

(2) INFORMATION FOR SEQ ID NO:28:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:28:

```
GCCACACAGC AAACCAGCAA GCAG                                              24

(2) INFORMATION FOR SEQ ID NO:29:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:29:

TGCTAGTGAG AAGGAAGCAG CTCTGT                                            26

(2) INFORMATION FOR SEQ ID NO:30:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:30:

CTCCAGGTTC ATGGCCCTTC CCGATG                                            26

(2) INFORMATION FOR SEQ ID NO:31:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:31:

CCATGCCCTG ACCTCTGTCC TCTCTA                                            26

(2) INFORMATION FOR SEQ ID NO:32:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:32:

TCGGCCTCCT TCCAGTTTCC ACTCCC                                            26
```

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:33:

TAGGGCCAGA CAGGTGAGGA CGGTGC                        26

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:34:

AACTCAGCCA CGGGCAGGGA GAGTG                        25

(2) INFORMATION FOR SEQ ID NO:35:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:35:

CCTAGTGAAA GGGAGCAGAC CAGGGC                        26

(2) INFORMATION FOR SEQ ID NO:36:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:36:

CTTTGCTTTC TCTGTGGGGC CACCTG                        26

(2) INFORMATION FOR SEQ ID NO:37:

(i) SEQUENCE CHARACTERISTICS:
        (A) LENGTH: 26 base pairs

-continued

```
        (B) TYPE: nucleic acid
        (C) STRANDEDNESS: single
        (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:37:

GTCCCCAGCA GTGCCCTGTC TCCCTG                                              26

(2) INFORMATION FOR SEQ ID NO:38:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: N (iv) ANTI-SENSE: N (xi) SEQUENCE DESCRIPTION: SEQ ID NO:38:

ACAGTCACTC CGTGGGCTAA GCGGGGG                                             27
```